(12) United States Patent
Wilchek et al.

(10) Patent No.: US 6,602,987 B1
(45) Date of Patent: Aug. 5, 2003

(54) AZOBENZENE DERIVATIVES AS LABELING AGENTS AND INTERMEDIATES THEREOF

(75) Inventors: Meir Wilchek, Rehovot (IL); Edward A. Bayer, Raanana (IL); Heike Hofstetter, DeKalb, IL (US); Margherita Morpurgo, Teolo (IT)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/831,494

(22) PCT Filed: Nov. 10, 1999

(86) PCT No.: PCT/IL99/00604

§ 371 (c)(1),
(2), (4) Date: Aug. 7, 2001

(87) PCT Pub. No.: WO00/27813

PCT Pub. Date: May 18, 2000

(30) Foreign Application Priority Data

Nov. 10, 1998 (IL) .................................................. 126991

(51) Int. Cl.⁷ .......................... C07K 17/06; C07K 1/13; C07C 245/08; G01N 33/532
(52) U.S. Cl. .................... 530/391.3; 435/6; 435/7.5; 435/7.92; 435/7.95; 436/544; 530/395; 530/409; 534/751; 534/843; 534/851; 534/852
(58) Field of Search .................... 435/7.92, 7.95, 435/7.5, 6; 436/544; 534/751, 851, 852, 843; 530/409, 391.3, 395

(56) References Cited

U.S. PATENT DOCUMENTS 5,182,203 A   1/1993   Ebersole et al.
5,492,803 A   2/1996   Landgrebe et al.

FOREIGN PATENT DOCUMENTS

DE   2 037 697      2/1971
WO   WO 97/00329    3/1997

OTHER PUBLICATIONS

Morpurgo et al (1998), "A Chemical Approach To Illustrate the Principle of Signal Transduction Cascades Using the Avidin—Biotin System", *J. Am. Chem. Soc.*, 120:12734–12739.

Tsurui Hironori, "PEG–Modified Avidin and Method for Separating Antigen or Antibody Using the Same", *Patent Abstracts of Japan*, Publ. No. 08012699, Publ. Date Jan. 16, 1996; vol. 1996, No. 5, May 31, 1996.

Green, M. "Avidin and Streptavidin", *Methods in Enzymology, US*, Academic Press Inc., San Diego, CA, vol. 184, Jan. 1, 1990, pp. 51–67.

*Primary Examiner*—Mary E. Ceperley
(74) *Attorney, Agent, or Firm*—Browdy and Neimark PLLC

(57) ABSTRACT

A compound of the formula I:

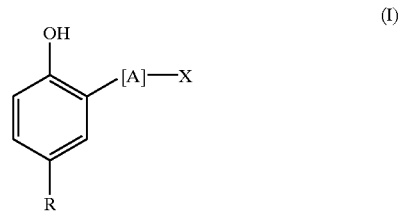

wherein R is H or —N═N-2-carboxyphenyl; A is $(CH_2)_n$ or —CH═CH—, wherein n is an integer from 0 to 10, or A may also be —CH(COOH)— when R is —N═N-2-carboxyphenyl; and X is a radical selected from the group consisting of: (i) Cl; (ii) $COOR_1$, wherein $R_1$ is p-nitrophenyl or N-succinimidyl; (iii) CONH—$NHR_2$, wherein $R_2$ is H, COO(t-butyl) or COObenzyl; (iv) CONH—[B]—$NHR_3$, wherein $R_3$ is H, $COOR_1$, or CO—[B']—maleimido, wherein $R_1$ is t-butyl, p-nitrophenyl or N-succinimidyl, and B and B', the same or different, are $(CH_2)_n$ wherein n is an integer from 2 to 10; (v) CONH—[B]—$COOR_4$, wherein $R_4$ is H, $C_1$–$C_8$ alkyl, N-succinimidyl; (vi) CONH—[B]—OH; (vii) CONH—[B]—CONH—$NHR_2$, wherein $R_2$ is H, COO(t-butyl) or COObenzyl; and (viii) $NHR_2$, wherein $R_2$ is H, COO(t-butyl) or COObenzyl, when A is —CH(COOH)— and R is —N═N-2-carboxyphenyl. The 4'-hydroxyazobenzene-2-carboxylic acid (HABA) compounds are novel reagents for labeling, isolation and detection of biological molecules.

9 Claims, 1 Drawing Sheet

AZOBENZENE DERIVATIVES AS LABELING AGENTS AND INTERMEDIATES THEREOF

CROSS-REFERENCE TO RELATED APPLICATIONS

The present application is the national stage under 35 U.S.C. 371 of international application PCT/IL99/00604, filed Nov. 10, 1999, which designated the United States, and which international application was published under PCT Article 21(2) in the English language. The entire contents of said PCT/IL99/00604 are hereby incorporated by reference.

FIELD OF THE INVENTION

The present invention relates to derivatives of 4'-hydroxyazobenzene-2-carboxylic acid (HABA) and to intermediates therefor, and to their use as novel reagents for labeling, isolation and detection of biological molecules.

BACKGROUND OF THE INVENTION

There are two major systems currently in use for the nonradioactive labeling of proteins and other biologically active molecules. These are the avidin-biotin system and the DIG (digoxygenin) system. In both cases, a reactive reagent, containing either the biotin or DIG moiety, is usually used for covalent coupling to a binding molecule, e.g. DNA, protein, etc, which in turn will recognize a target molecule. Once biotin or DIG is thus incorporated into the experimental system, avidin or DIG-specific antibody (anti-DIG) is applied subsequently to serve as a bridge between the target and a probe that is required for a desired purpose such as for detection, localization, quantification, isolation, etc.

Both avidin-biotin and the DIG systems suffer from a series of disadvantages. One of the main problems of the avidin-biotin system is that biotin is a natural vitamin, and as such, it is a normal component of cells either in the free state or covalently bound to a group of biotin-dependent enzymes. Thus, the presence of free biotin will interfere with the targeting of avidin to a biotinylated molecule, whereas the presence of biotin-dependent enzymes will result in specific but unwanted binding of avidin. A second disadvantage with the avidin-biotin system is that in some cases a reversible binding between avidin and biotin would be desirable, whereas the extremely high affinity essentially results in an irreversible binding. Another problem involves the analysis and processing of a biotinylated preparation. Specifically, since biotin is not chromogenic, it is difficult to quantify the number of biotin moieties per molecule and, more relevant, to determine the percentage of molecules which failed to undergo biotinylation. In this context, it is not easy to separate between biotinylated and non-biotinylated molecules, after the biotinylation step.

The DIG:anti-DIG system also suffers from a set of disadvantages. First, it has been noted that DIG reacts nonspecifically with antibodies from serum. Like biotin, the lack of chromophore renders it difficult to determine the amount of DIG-labeled molecules and to separate them from the unlabeled fraction.

Both systems suffer from another major drawback in that only one type of protein is available for detection, i.e. avidin or streptavidin for binding biotin and anti-DIG for DIG.

SUMMARY OF THE INVENTION

It is an object of the present invention to provide new labeling reagents based on derivatives of the azo dye HABA (4'-hydroxyazobenzene-2-carboxylic acid).

The present invention relates to compounds of the formula I:

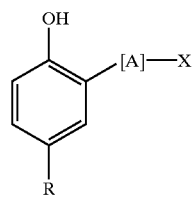

wherein
R is H or —N=N-2-carboxyphenyl;
A is $(CH_2)_n$ or —CH=CH—, wherein n is an integer from 0 to 10, or
A may also be —CH(COOH)— when R is —N=N-2-carboxyphenyl; and
X is a radical selected from the group consisting of:
(a) Cl;
(b) $COOR_1$, wherein $R_1$ is p-nitrophenyl or N-succinimidyl;
(c) CONH—$NHR_2$, wherein $R_2$ is H, COO(t-butyl) or COObenzyl;
(d) CONH—[B]—$NHR_3$, wherein $R_3$ is H, $COOR_1$, or CO—[B']-maleimido, wherein $R_1$ is t-butyl, p-nitrophenyl or N-succinimidyl, and B and B', the same or different, are $(CH_2)_n$ wherein n is an integer from 2 to 10;
(e) CONH—[B]—$COOR_4$, wherein B is as defined in (iv) above and $R_4$ is H, $C_1$-$C_8$ alkyl, N-succinimidyl;
(f) CONH—[B]—OH, wherein B is as defined in (iv) above;
(g) CONH—[B]—CONH—$NHR_2$, wherein B is as defined in (iv) above and $R_2$ is H, COO(t-butyl) or COObenzyl; and
(h) $NHR_2$, wherein $R_2$ is H, COO(t-butyl) or COObenzyl, when A is —CH(COOH)— and R is —N=N-2-carboxyphenyl.

The HABA compounds of formula I, wherein R is —N=N-2-carboxyphenyl, are obtained from the corresponding non-azo compounds wherein R is H.

In one embodiment, A is $(CH_2)_n$ and n is 2 to 4, preferably 2, and the compounds wherein R is H are derivatives of 3-(2-hydroxyphenyl)-propionic acid (derivatives (ii) above),-propionamide (derivatives (iv) to (vii) above) and propionic acid hydrazide (derivatives (iii) above). In another embodiments, B is preferably $(CH_2)_5$ or $(CH_2)_6$ and B' is preferably $(CH_2)_3$.

The present invention further relates to conjugates of HABA itself or of a HABA compound of formula I with a carrier (herein HABAylated compounds), wherein said carrier is a protein or polypeptide, an amino-carrying polymer, a polynucleotide, an oligonucleotide, a polysaccharide, an oligosaccharide or a compound containing a sugar molecule such as glycocoproteins. Thus the invention encompasses HABAylated cytokines, antibodies, hormones, receptors, DNA, DNA probes, oligonucleotides and other HABAylated molecules.

In another aspect, the present invention provides anti-HABA antibodies, both polyclonal and monoclonal, which are prepared by immunization of rabbits and mice, respectively, with a conjugate of HABA and an immunogenic protein, such as for example HABA-KLH.

The HABA derivatives of formula I can be used as labeling reagents. Labeled molecules are amenable to interaction with either avidin or HABA-specific antibodies (anti-HABA) and can be used in several applications including, but not being limited to, isolation (affinity chromatography) and detection (immunoassay) of biologically active molecules.

The invention further provides a method for localization, quantitation and isolation of molecules I in a sample which comprises contacting the sample with a HABAylated molecule II that recognizes molecule I, and then reacting with labeled anti-HABA antibodies or labeled avidin. The HABAylated molecule II such as an HABAylated antibody, lectin, DNA or RNA, is added to a sample such as a cell preparation, a DNA or protein blot containing the target molecule II, e.g. the antigen, the carbohydrate, etc, the excess of HABAylated probe is removed after formation of the HABAylated binder II/target molecule I complex and then reacted with labeled anti-HABA antibodies or labeled avidin.

The HABA system has many advantages over both the avidin-biotin and the DIG/anti-DIG systems, as follows:

HABA can be detected by two unrelated systems: avidin and anti-HABA. Interestingly, the interaction between HABA and anti-HABA generates a spectral shift similar to that of the HABA-avidin interaction from 350 to 500 nm. Anti-HABA fails to recognize biotin.

The HABA moiety is easily detectable and quantifiable, owing to its inherent chromophore and spectral shift upon binding to avidin or anti-HABA.

It is easy to separate between HABAylated and non-HABAylated molecules, due to the reversible interaction with avidin.

HABAylated molecules can be recognized by avidin and, after addition of biotin, the HABAylated molecule is then again available for detection by anti-HABA antibodies.

EXAMPLES

Figure 1:
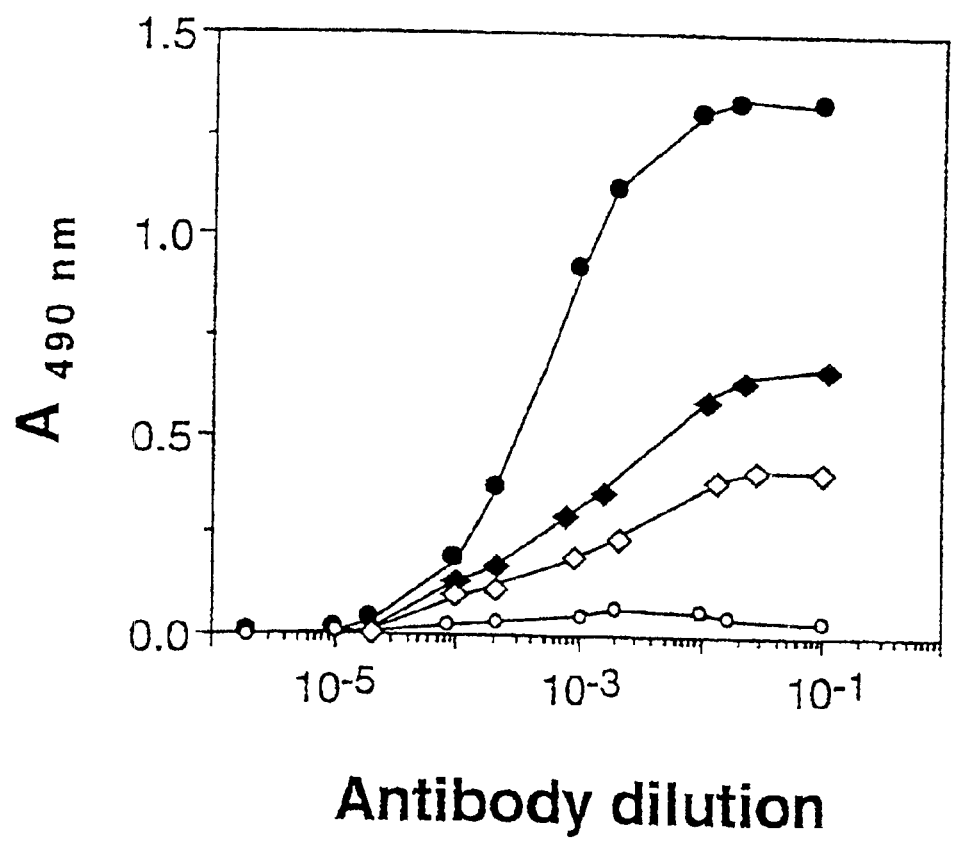
FIG. 1 shows the results of ELISA assay using the polyclonal affinity-purified anti-HABA antibody. Plates were coated with HABAylated avidin, the desired dilutions of antibodies were applied with biotin (♦ Antibody purified on column A, ● Antibody purified on column B) or without biotin (◇ Antibody purified on column A, ○ Antibody purified on column B) and the plates were assayed using a secondary antibody-enzyme conjugate.

The invention will now be illustrated by the following non-limiting Examples.

LIST OF COMPOUNDS

In the Examples, the following compounds 1–29, which formulas are presented in Appendix I hereinafter just before the Claims, will be identified by their numbers in bold:
0. 4'-hydroxyazobenzene-2-carboxylic acid (HABA)
1. 3-(2-hydroxyphenyl)propionic acid
2. N-succinimidyl 3-(2-hydroxyphenyl)propionate
3. N-6-(t-butoxycarbonylamino)hexyl 3-(2-hydroxyphenyl) propionamide
4. N-6-aminohexyl 3-(2-hydroxyphenyl)propionamide
5. N-6-(succinimidyloxycarbonylarino)hexyl 3-(2-hydroxyphenyl)propionamide
6. N-6-(maleimidopropylcarbonylamino)hexyl 3-(2-hydroxyphenyl)propionamide
7. N-6-(methoxycarbonyl)pentyl 3-(2-hydroxyphenyl) propionamide
8. N-5-carboxyphenyl 3-(2-hydroxyphenyl)propionamide
9. N-t-butoxycarbonylamino 3-(2-hydroxyphenyl) propionamide
10. N-6-hydroxyphenyl 3-(2-hydroxyphenyl)propionamide
11. N-5-(succinimidyloxycarbonyl)pentyl 3-(2-hydroxyphenyl)propionamide
12. N-5-(t-butoxycarbonylhydrazinocarbonyl)pentyl 3-(2-hydroxyphenyl)propionamide
13. 3-(2-hydroxyphenyl)propionic acid hydrazide
14. N-5-hydrazinocarbonylpentyl 3-(2-hydroxyphenyl) propionamide
15. 3'-(6-t-butoxycarbonylamino)hexylaminocarbonylethyl-4'-hydroxy-azobenzene-2-carboxylic acid
16. 3'-(6-aminohexylaminocarbonylethyl)-4'-hydroxy-azobenzene-2-carboxylic acid
17. 3'-(6-(succinimidyloxycarbonylamino) hexylaminocarbonylethyl)4'-hydroxy-azo-benzene-2-carboxylic acid
18. 3'-(6-(maleimidopropylcarbonylamino) hexylaminocarbonylethyl)-4'-hydroxy-azobenzene-2-carboxylic acid
19. 3'-(1'-carboxy-t-butoxycarbonylaminomethyl)-4'-hydroxy-azobenzene-2-carboxylic acid
20. 3'-(5-carboxypentylaminocarbonylethyl)-4'-hydroxy-azobenzene-2-carboxylic acid
21. 3'-(5-succinimidyloxycarbonylpentylaminocarbonylethyl)-4'-hydroxy-azobenzene-2-carboxylic acid
22. 3'-(5-t-butyloxycarbonylhydrazinocarbonylpentylamino carbonylethyl)-4'-hydroxy-azobenzene-2-carboxylic acid
23. 3'-(t-butyloxycarbonylhydrazinocarbonylethyl)-4'-hydroxy-azobenzene-2-carboxylic acid
24. 3'-(6-hydroxyhexylaminocarbonylethyl)-4'-hydroxy-azobenzene-2-carboxylic acid
25. 3'-(5-(hydrazinocarbonyl)pentylaminocarbonylethyl)-4'-hydroxy-azobenzene-2-carboxylic acid
26. 3'-(hydrazinocarbonylethyl)-4'-hydroxy-azobenzene-2-carboxylic acid
27. 3'-(carboxyethyl))-4'-hydroxy-azobenzene-2-carboxylic acid
28. 3'-(succinimidyloxycarbonylethyl)-4'-hydroxy-azobenzene-2-carboxylic acid
29. 3'-(1-carboxy-1-amino-methyl)-4'-hydroxy-azobenzene-2-carboxylic acid ABBREVIATIONS: BOC: t-butoxycarbonyl; BSA: bovine serum albumin; DCC: N,N'-dicyclohexylcarbodiimide; DMAP: dimethylaminopyridine; DMF: N,N'-dimethyl formamide; DSC: disuccinimidylcarbonate; HABA: 4'-hydroxyazobenzene-2-carboxylic acid; KLH: Keyhole Lympet Hemocyanin; NHS: N-hydroxysuccinimide; Su: succinimidyl; TEA: triethylamine; TSTU: tetramethyluronium tetrafluoroborate.

REAGENTS and INSTRUMENTATION: DCC and TEA were obtained from Merck (Darmstadt, Germany). N-BOC-1,6-diaminohexane, N-BOC-1,6-diaminoetane, ε-aminocaproic acid and 6-aminohexanol, were obtained from FLUKA Chemie (Buchs, Switzerland). DSC was purchased from Calbiochem/NovaBiochem (La Jolla, Calif., USA). 3-(2-hydroxy-phenyl)propionic acid, 2-hydroxycinnarmic acid, anthranilic acid and anhydrous hydrochloric acid solution in dioxane were purchased from Aldrich (Milwaukee, Wis., USA). KLH was gently provided by Biomakor (Israel), Avidin was provided by STC Laboratories (Winnipeg, Canada). β-Maleimidopropionic acid N-hydroxysuccinimidyl ester, N-hydroxy-succinimide, biotin, DL-O-tyrosine, HABA, BSA, and all the other chemicals were obtained from Sigma Chemicals (S.Louis, Mo., USA). Sepharose CL-4B was purchased from Pharmacia Biotech AB (Uppsala, Sweden). BCA protein assay reagent was obtained from Pierce (Rockford, Ill., USA). Peroxidase-conjugated AffiniPure Goat Anti-Mouse IgG (H+L) and anti-rabbit IgG were obtained from Jackson ImmunoResearch Laboratories (West Grove, Pa., USA). UV spectra were recorded with a Milton Roy Spectronic UV-Vis Spectrophotometer, mod. 1201.

Methods of Synthesis of 3-(2-Hydroxyphenyl) propionic Acid Derivatives (Compounds 2–14) and of the HABA Derivatives (Compounds 15–29)

The methods of synthesis of compounds 2–29 are depicted in Schemes 1–8 hereinafter just before the Claims, and are summarized as follows:

(i) The HABA derivatives are prepared by diazotization of the 3-(2-hydroxyphenyl)-propionic acid derivatives with anthranilic acid and sodium nitrite according to standard procedures.

(ii) Compounds containing a Su—O—CO—[A]— or a Su—O—CO—[B]— group are prepared from the corresponding free carboxylic acids either by activation with NHS or with TSTU, according to procedures a and b, respectively, in Scheme 1. Thus, for example, Compounds 2, 11, 21, 28, are obtained by reaction of Compounds 1, 8, 20, 27, respectively, either with (a) NHS in the presence of DCC, or (b) with TSTU and DMAP.

(iii) Compounds containing a BOC—NH—[B]—NH— group such as for example, Compound 3, are prepared by reaction of the corresponding Su—O—CO—[A]— compounds obtained as in (ii) above, for example Compound 2, with a BOC—NH—[B]—NH$_2$ compound as shown in Scheme 2A. The HABA derivative such as for example Compound 15, can then be prepared by diazotization, as depicted in Scheme 2B.

(iv) Compounds containing a H$_2$N—[B]—NH— group such as for example, Compounds 4 and 16, are prepared by removal of the protective BOC group from the corresponding BOC—NH—[B]—NH— compounds obtained as in (iii) above, for example from Compounds 3 and 15, respectively (Scheme 2B).

(v) Compounds containing a Su—O—CO—NH—[B]—NH— group such as for example, Compounds 5 and 17, are prepared by reaction of the corresponding H$_2$N—[B]—NH— compounds obtained as in (iv) above, for example Compounds 4 and 16, respectively, with DSC in the presence of TEA (Scheme 2C).

(vi) Compounds containing a maleimido-[B']—CO—NH—[B]—NH— group such as for example, Compounds 6 and 18, are prepared by reaction of the corresponding H$_2$N—[B]—NH— compounds obtained as in (iv) above, for example Compound 4 and 16, with N—Su 3-maleimidopropionate in the presence of TEA, according to Scheme 3.

(vii) Compounds containing an alkyl-O—CO—[B]—NH— group such as for example, Compound 7, are prepared by reaction of the corresponding free carboxylic acids, for example Compound 1, with an ω-aminoalkanoic acid ester alkyl-O—CO—[B]—NH$_2$, in the presence of DCC/TEA.

(viii) Compounds containing a HOOC—[B]—NH— group such as for example Compound 8, are prepared by hydrolysis of the corresponding esters alkyl-O—CO—[B]—NH— obtained as in (vii), for example from Compound 7.

(ix) Compounds containing a BOC—NH—NH—CO—[A]— or BOC—NH—NH—CO—[B]— group such as for example, Compounds 9 and 12, respectively, are prepared by reaction of the corresponding Su—O—CO—[A]— or Su—O—CO—[B]— compound, for example Compounds 2 and 11, respectively, with BOC-hydrazine. The HABA derivatives such as for example Compounds 22 and 23, can then be prepared by diazotization from Compounds 12 and 9, respectively.

(x) Compounds containing a HO—[B]—NH—CO—[A]— group such as for example, Compound 10, are prepared by reaction of the corresponding Su—O—CO—[A]— compound, for example Compound 2, with a HO—[B]—NH$_2$ compound. The HABA derivative such as for example Compound 24, can then be prepared by diazotization from Compound 10.

(xi) Compounds containing a H$_2$N—NH—CO—[A]— or H$_2$N—NH—CO—[B]—NH— group such as for example, Compounds 13 and 14, respectively, and the HABA derivatives 26 and 25, respectively, are prepared by removal of the protective BOC group from the corresponding BOC—NH—NH—CO—[A]— or BOC—NH—NH—[B]—NH— compounds obtained as in (ix) above, for example Compounds 9 and 12, and Compounds 22 and 23, respectively.

Example 1

Synthesis of Derivatives of 3-(2-Hydroxyphenyl) propionic Acid 1.1 Synthesis of Compound 2

According to method (ii) above, to a cooled solution of Compound 1 (0.997 g, 6 mmoles) in CH$_2$Cl$_2$ (21 ml), NHS (0.828 g, 7.2 mmoles) and DCC (1.485 g, 7.2 mmoles) were added. After 3.5 h, the solution containing Compound 2 was filtered and directly used for the next synthetic step, without any further purification.

1.2 Synthesis of Compound 3

According to method (iii) above, N1-BOC-1,6-diaminohexane (1.52 g, 6 mmoles) was added, while stirring, to the dichloromethane solution of Compound 2, followed by 835 ml (6 mmoles) of TEA. The reaction was stirred overnight at room temperature, filtered and evaporated to dryness. The product was redissolved in ethyl acetate and the organic solution was washed (with diluted NaHCO$_3$, diluted citric acid and water), dried over Na$_2$SO$_4$ and evaporated to dryness. Diethyl ether (30 ml) was added to the resulting oil, the precipitated impurities were removed by filtration, and the solution containing Compound 3 was evaporated to dryness and used further.

1.3 Synthesis of Compound 4

According to method (iv) above, Compound 3 (1 g) dissolved in dioxane (40 ml) was treated with HCl-saturated dioxane. After one hour, the precipitate containing Compound 4 was filtered, washed with diethyl ether and dried.

1.4 Syntizesis of Compound 5

According to method (v) above, a solution of Compound 4 (0.5 mmoles) in DMF (1.6 ml) was slowly added in portions (8×200 ml), while stirring, to a DSC solution in CH$_3$CN (256 mg, 1 mmole, in 10 ml). After each addition, 2 equivalents of TEA (with respect to compound 4) were also added, and the pH monitored continuously and maintained below 4.0. Five minutes after the last addition of Compound 4, 5 ml of IN HCl were added. The product Compound 5 crystallized as a fine powder, was isolated by filtration, washed with diluted HCl and dried.

1.5 Synthesis of Compound 6

According to method (vi) above, Compound 4 dissolved in DMF (0.05 mmoles in 500 ml) was added to a solution of N-succinimidyl 3-maleimido propionate (26.6 mg, 0.1 mmole) in 1.5 ml CH$_3$CN/DMF 3:1, followed by 0.1 mmoles TEA. After 2 hours, 3 ml of H$_2$O were added and, after acidification with 1N HCl, the product Compound 6 crystallized.

1.6 Synthesis of Compound 7

According to method (vii) above, to a solution of Compound 1 (0.997 g, 6 mmol) in CH$_2$Cl$_2$ (25 ml) were added ε-aminocaproic acid methyl ester (1.74 g, 12 mmol), an equimolar amount of TEA (1.6 ml, 12 mmol) and DCC (1.36 g, 6.6 mmol). The reaction was carried out for 4 hours in an ice bath. The solution was washed thoroughly with water, HCl (0.05 M), water, bicarbonate (0.1 M) and again with water. The $CH_2Cl_2$ fraction was dried over sodium sulfate and the pure product Compound 7 was obtained by precipitation with absolute diethylether.

1.7 Synthesis of Compound 8

According to method (viii) above, Compound 7 (330 mg, 1.08 mmol) was dissolved in methanol and 5.4 ml 0.5 M NaOH were added thereto. After 1 hour, the reaction mixture was brought to pH 2 with HCl and the methanol removed by evaporation. The oily mixture was dissolved in hot ethyl acetate and the pure product Compound 8 crystallized upon cooling down.

1.8 Synthesis of Compounds 9 and 12

According to method (ix) above, Compounds 9 and 12 were synthesized from Compounds 2 and 11, respectively, by reaction with BOC-hydrazine, according to the procedure described in section 1.2 above for the preparation of compound 3.

1.9 Synthesis of Compound 11

According to method (ii) above, Compound 11 was obtained from compound 8, using the same procedure described in section 1.1 above for the preparation of compound 2.

1.10 Synthtesis of Compound 10

According to method (x) above, Compound 10 was obtained from compound 2 and 6-aminohexanol, using the same procedure described in section 1.2 above for the preparation of compound 3.

1.11 Synthesis of Compounds 13 and 14

According to method (xi) above, Compounds 13 and 14 were obtained by removing the BOC protective group from Compounds 9 and 12, respectively, using the same procedure described in section 1.3 above for the preparation of Compound 4.

Example 2

Synthesis of HABA-derivatives 2.1 Synthesis of Compound 15 (HABA-$C_2$-CONH$C_6$—NH—BOC)

According to method (i) above, to cooled anthranilic acid (0.750 g, 5.45 mmoles) and $NaNO_2$ (0.377 g, 5.45 mmoles) dissolved in water (15 ml), 1.5 ml of concentrated HCl were added. After 10 min, the solution was dropwise added to Compound 3 (1.62 g, 5.45 mmoles) dissolved in a mixture of methanol/0.5M KOH:1/1 (15 ml). The pH was controlled and adjusted to 8.0 using HCl and KOH. After 20 min, methanol was removed by evaporation, the solution was acidified to pH 3–4 with diluted citric acid, and the solid product was extracted with ethyl acetate. The organic solution was washed with water, dried over $Na_2SO_4$ and evaporated to dryness, thus obtaining Compound 15.

2.2 Synthesis of Compound 16 (HABA-$C_2$CONH—$C_6$—$NH_2$xHCl)

According to method (iv) above, a solution of Compound 15 in dioxane was dried, filtered, and HCl saturated dioxane was added. After 1 hour, the product Compound 16 precipitated as the hydrochloride salt, was isolated by filtration, washed with diethyl ether and dried.

2.3 Synthesis of Compound 17 (HABA-$C_2$—CONH—$C_6$—NH—OSu)

According to method (v) above, a solution of Compound 16 (35.8 mg, 0.08 mmoles) in DMF (0.24 ml) was slowly added into portions (8×30 µl), while stirring, to a solution of DSC (41 mg, 0.16 mmoles) in $CH_3CN$ (1.6 ml). After each addition, 2 equivalents of TEA (with respect to Compound 16) were also added, and the pH monitored continuously and maintained below 4.0. Five minutes after the last addition of the HABA-derivative 16, 2 ml of 1N HCl were added. The product Compound 17 crystallized as a fine powder. It was isolated by filtration, washed with diluted HCl and dried.

2.4 Synthtesis of Compound 18 (HABA-$C_2$—CONH—$C_6$—NHCO—$C_3$—N-Maleimide)

According to method (vi) above, N-succinimidyl 3-maleimidopropionate (31.5 mg) was dissolved in 2 ml of $CH_3CN$/DMF 3/1. Compound 16 was dissolved in DMF (25 mg in 500 ml) and then added to the maleimido derivative solution, followed by 21 ml of TEA. After 3 hours, 5 ml of $H_2O$ were added and, after acidification with 1N HCl, the product Compound 18 crystallized.

2.5 Synthesis of Compounds 19, 20, 22, 23, 24, 27

Compounds 19, 20, 22, 23, 24, 27 were synthesized from the Compounds N-BOC-DL-o-tyrosine, 8, 12, 9, 10 and 1, respectively, following the same procedure described in section 2.1 above for Compound 15.

2.6 Synthesis of Compounds 25 and 26

According to method (xi) above, Compounds 25 and 26 were obtained from Compounds 23 and 22, respectively, by acid hydrolysis, following the same procedure described in section 2.2 above for Compound 16.

2.7 Synthesis of Compound 21

According to method (ii) above, Compound 21 was prepared from Compound 20 by two different procedures:

a. Activation with NHS (Scheme 1a)

The synthesis was carried out using the same procedure described in Example 1.1 above for Compound 2. Compound 20, DCC/$CH_2Cl_2$ and NHS were used in equimolar concentrations to avoid activation of the carboxyl group at the second phenyl ring. The urea derivative was removed by filtration, and Compound 21 was washed with water and dried.

b. Activation with TSTU (Scheme 1b) (Bannwarth 1991)

TSTU (70.4 mg, 0.24 mmol) and DMAP (57 mg, 0.48 mmol) were added to Compound 20 (100 mg, 0.24 mmol) dissolved in a mixture of DMF/dioxane/water (1/1/0.5). After complete conversion (30 min), Compound 21 (purity 96%) was lyophylized and further purified by HPLC.

2.8 Synthesis of Compound 28

According to method (ii) above, Compound 28 was prepared from Compound 27 by two different procedures:

a. Activation with NHS (Scheme 1a)

The synthesis was carried out as described in section 2.7.a above for Compound 21.

b. Activation with TSTU (Scheme 1b) (Bannwarth 1991).

TSTU (100 mg, 0.32 mmol) and DMAP (80 mg, 0.64 mmol) were added to Compound 27 (100 mg, 0.32 mmol) dissolved in a mixture of DMF/dioxane/water (1/1/0.5). Complete conversion occurred after 30 minutes. Compound 28 (purity 95%) was lyophylized and further purified by HPLC.

2.9 Synthesis of Compound 29

Compound 29 was obtained from Compound 19 upon acidic cleavage of the BOC group, following the same procedure described in section 2.2 for Compound 16.

2.10 Synthesis of Further HABA-derivatives

HABA-derivatives carrying different spacers A are obtained by the same procedures described above but using different derivatives as starting materials instead of 3-(2-hydroxyphenyl)propionic acid (Compound 2). For example, compounds wherein A is CH=CH are obtained using 2-hydroxycinnarmic acid derivatives as starting materials; when A is $(CH_2)_n$ and n is zero, from salicylic acid derivatives; when n=1, from 2-hydroxyphenylacetic acid derivatives; when n=3, from 4-(2-hydroxyphenyl)butyric acid derivatives; and when n>3, from X-(2-hydroxyphenyl) acid derivatives (X=n+1) with the desired (n) chain length. These acids can be obtained by malonic synthesis as described in Beil. III, 10, 586–587 for the butyric acid derivatives.

Example 3

Labeling of Proteins and Other Compounds with HABA

3.1 Chemistry of Binding

The 2-hydroxyphenyl- or HABA-derivatives that have been activated as N—Su carbaamates (—NH—CO—O—Su) or as N—Su esters (—CO—O—Su) react with primary amino groups at the level of any protein, peptide or amino-carrying polymer (e.g. Sepharose-diaminohexane, etc.) surface. In proteins or peptides, the binding occurs through the lysyl-ε-$NH_2$ or the α-$NH_2$ of the first amino acid of the chain. The coupling reactions are depicted in Schemes 4 and 5 and lead to urea and carbamide types of bond, respectively.

The 2-hydroxyphenyl- or HABA-derivatives functionalized with a terminal maleimido group are thiol-specific reagents. In proteins or peptides, the binding occurs at the level of cysteine SH functions. The reaction is depicted in Scheme 6.

The 2-hydroxyphenyl- or HABA-derivatives functionalized with a terminal hydrazido group react with any aldehyde residue. In proteins, glycoproteins and carbohydrates in general, the reaction occurs, after periodate or enzymatic oxidation, at the level of the sugar aldehydic residues. The reaction is depicted in Scheme 7.

3.2 Protein Modification with HABA Reagents (HABAylated Proteins)

3.2.a Succidimyl Esters (Compounds 21 and 28)

In a general coupling reaction according to Scheme 5, a freshly prepared solution of a HABA-N—Su ester (—CO—O—Su, 2.5 ml) in EtOH:PBS 1:3 (1–50 mg/ml) is added, while stirring, to a solution of a protein P—$NH_2$ (2–20 mg) in 1 ml of phosphate buffer, pH 7.4 containing 0.5M NaCl. The protein P—$NH_2$ is, for example, a protein to be used for detection as a binder, e.g. an antibody. The molar ratio between the HABA-N—Su ester derivative and the protein is between 4 and 100 depending on the starting protein concentration, the reactivity of the specific protein and the desired degree of modification. The reaction is carried out at room temperature or lower for several hours. Examples of HABAylation procedures using succinimidyl esters 21 and 28 are shown and summarized in Table 1 for several proteins.

TABLE 1

HABAylation of proteins-Reaction conditions and products obtained.

| Protein | Protein conc. in coupling (mg/ml) | HABA/protein used and react. Time | HABA/protein Obtained with Comp. 21 & 28 | residual activity % |
|---|---|---|---|---|
| BSA | 10 | 16(12 h) | 2/2 | — |
|  | 10 | 40(12 h) | 4/5 | — |
| KLH | 1 | 300(12 h) | 282/400 | — |
|  | 1 | 300(1/2 h.) | 118/256 | — |
| Ribonuclease | 10 | 4(12 h) | 1/0.5 | — |
|  | 10 | 30(2 h) | 3/2.5 | — |
| γ-Globulin | 1 | 345(2 h) | 7/11 | — |
|  | 1 | 100(2 h) | 5/8.5 | — |
| Lysozyme | 10 | 4(12 h) | 1/1 | — |
|  | 10 | 30(2 h) | 2.5/2 | — |
| L-Lactalbumin | 10 | 40(1 h) | 2/1 | — |
| Sheep anti-rabbit IgG | 2.3 | 150(12 h) | 16/12 | 100 |
|  | 2.3 | 150(1/2 h.) | 9/7 | 100 |
| Mouse IgG | 17 | 200(1/2 h.) | 7/5 | 100 |
| Anti-L-amino acids | 2 | 100(1/2 h.) | 19/14 | 98 |
|  | 2 | 50(1/2 h.) | 11/6 | 100 |

The coupling was carried in phosphate buffer containing 0.5M NaCl, pH 7.4.

3.2.b Succinimidyl Carbamates (Compound 17)

In a general coupling reaction according to Scheme 4, 10–50 ml of a concentrated solution of a HABA-Su carbamate (—NH—CO—O—Su) in DMF (5–30 mg/ml) are added, while stirring, to a solution of a protein P—$NH_2$ in aqueous buffer at pH 8.0–8.5 (2–10 mg/ml). The protein P—$NH_2$ is, for example, a protein to be used for detection as a binder, e.g. an antibody. The molar ratio between the HABA-Su carbamate derivative and the protein is between 50 and 400, depending on the starting protein concentration, the reactivity of the specific protein and the desired degree of modification. The reaction is carried out at room temperature or lower for 1–2 hours. Examples of HABAylation procedures, reaction conditions and products using succinimidyl carbamates (Compound 17) are shown and summarized Table 2 for several proteins.

TABLE 2

HABAylation of proteins-Reaction conditions and products obtained

| protein | Protein conc. in coupling (mg/ml) | HABA/protein used and react. time | HABA/protein obtained with Comp. 17 | residual activity % |
|---|---|---|---|---|
| Goat-anti-Mouse IgG | 3.19 | 50(1 h.) | 6 | 100 |
|  | 3.19 | 100(1 h.) | 6.5 | 100 |
|  | 3.19 | 200(1 h.) | 8 | 90 |
|  | 3.19 | 400(1 h.) | 11 | 85 |
| Ovoalbumin | 2.5 | 20(1/2 h.) | 0.5 | — |
|  | 9.9 | 20(1/2h.) | 2 | — |
| KLH | 10 | 300(1/2 h.) | 51 | — |
|  | 50 | 60(1/2 h.) | 20 | — |
|  | 60 | 15(1/2 h.) | 1.5 | — |
| BSA | 5 | 150(24 h) | 20 | — |
|  | 5 | 150(24 h) | 16 | — |
| HRP | 2 | 300(2 h) | 3 | 100 |
|  | 7.7 | 35(3 h) | 0.5 | 100 |

Coupling was carried out in phosphate buffer adjusted to pH 8.5 with a few drops of 4% $NaHCO_3$.

3.2.c Maleimido derivatives (Compound 18)

According to Scheme 6, HABAylation of cysteine residues in proteins and peptides P-SH is carried out by a coupling reaction with maleimido derivatives, either using an excess of peptide, thus obtaining a mixture of HABAylated and non-HABAylated products, or using a large excess of the HABA reagent, in which case complete HABAylation is obtained.

For HABAylation of glutathione, 50 ml of a HABA-maleimide solution in methanol (20 mg/ml) were mixed with 2 mg of GSH, previously dissolved in 2 ml of PBS. After 5 min, total disappearance of the maleinido reagent can be verified by TLC ($CHCl_3$/MeOH 20%).

For HABAylation of the single cystein residue (Cys 62) of Cellulose Binding Domain (CBD) from *Clostridium Thermocellum* YS, a solution of the HABA-maleimide reagent in methanol is added to a solution of CBD in PBS in a 2 fold excess.

3.2.d HABA-hydrazido Derivatives (Compounds 25 and 26)

According to Scheme 7, aldehyde residues of glycoproteins and polysaccharides are modified using protocols described elsewhere (Wilchek and Bayer, 1987).

3.2.e Protein Modification with 3-(2-Hydroxyphenyl) propionic Acid Derivatives (Compounds 2, 5, 6, 11, 13, 14)

Proteins can be modified with 3-(2-hydroxyphenyl) propionic acid derivatives by similar procedures as described in 3.2.a–3.2.d above according to Schemes 5, 6 and 7 (R=H).

3.3 Purification of the HABAylated Proteins

The products according to 3.2.a–3.2.e above are purified from low molecular weight molecules such as excess of reagent and NHS in the case of succinimidyl reagents, by overnight dialysis at 4° C. or by gel filtration on a G25 column. In this case, 3 mg of protein mixture are applied to a column of diameter 0.5 cm×h: 20 cm, and PBS or any desired buffer is used as eluant.

If the final reaction mixture of any HABAylation contains both non-HABAylated and HABAylated products, the two fractions can be separated by affinity chromatography using a Sepharose-avidin column that retains the HABAylated molecules. A highly protein concentrated Sepharose-avidin gel (5 mg avidin/g wet gel), prepared by cyanogen bromide or other activation method as described by Wilchek et al, 1984, is used for this purpose. PBS is used as washing buffer to elute the unmodified fraction from the gel. The retained protein or peptide is then eluted with HABA, biotin, salts or 50 mM, pH 10.5 TEA, depending on the amount of HABAylation. When the basic elution is carried out, fractions are immediately neutralized using 0.2 M acetic acid. If biotin solution is used to elute the HABAylated molecule, the avidin column will have to be treated under conditions which dissociate avidin and biotin.

3.4 Characterization of the HABAylated Proteins

3.4.a Protein Concentration and Degree of HABAylation

Protein concentration after coupling and purification is estimated by BCA (bicinchoninic acid) protein assay (Pierce) or by using the UV absorption values and keeping into account the influence of the HABA residues at 280 nm ($\epsilon$280 nm for compound 16=3,300). The degree of modification is calculated, after purification from side-products, on the basis of UV absorption at 356 nm in PBS, at 415 nm in basic environment, or at 504 nm after addition of excess of avidin in PBS.

TABLE 3

Spectroscopic characteristics of HABA (Compound 0) in different conditions.

| Conditions | $\lambda$max (nm) | $\epsilon[cm^{-1}M^{-1}]$ |
|---|---|---|
| PBS | 350 | 20,500 |
| +affinity purified anti-HABA in PBS, (1:1) | 482 | 50,000 |
| +Avidin in PBS, (20:1) | 500 | 35,500 |

In the case of proteins containing chromophores, e.g. KLH, which has a chromophore with a maximum of absorption at 344 nm, absorption of the native protein has to be taken into account in all calculations.

3.4.b Interaction of Avidin and anti-HABA Antibodies with HABA-derivatives

Interaction of the HABAylated proteins with avidin or with anti-HABA antibodies is verified by following the characteristic shift of the absorption of the HABA chromophore. Table 4 depicts the spectroscopic characteristics in the spectra range of the HABA-derivatives as free molecules (not bound to proteins) upon interaction with avidin or specific affinity purified antibodies.

TABLE 4

Molar Extinction Coefficients for HABA-derivatives

| Compound | Buffer/conditions | $\lambda$max (nm) | $\epsilon[cm^{-1}M^{-1}]$ at $\lambda$max |
|---|---|---|---|
| 16 | PBS | 356 | 12,900 |
| 16 | 0.1 M AcOH | 356 | 12,500 |
| 16 | 0.1 M NaOH | 420 | 15,000 |
| 16 | PBS/AVIDIN | 504 | 30,000 |
| 16 | PBS/anti-HABA | 482 | 50,000 |
| 17 | 0.1 M AcOH | 356 | 12,200 |
| 27 [A] = (CH=CH) | PBS | 356 | 15,500 |
| 27 [A] = (CH=CH) | PBS/AVIDIN | 520 | 33,000 |
| 27 [A] = (CH=CH) | PBS/ anti-HABA | 505 | 50,000 |

Example 4

HABA-Sepharose with High Degree of Functionalization

A high degree of Sepharose HABAylation can be obtained by using the synthetic approach described in Scheme 8. The gels obtained are intensely colored in dark red and have a high affinity and capacity for avidin (~20 mg/g wet gel). On the other hand, proteins such as those contained in the egg yolk, e.g. ovalbumin, ovomucoid, conalbumin, riboflavin-binding protein and lysozyme, are not retained by the gels. HABA-Sepharose can therefore be used to extract avidin from any solution or for its purification from egg yolk.

The HABA-Sepharose column can also be applied for affinity purification of polyclonal anti-HABA antibodies from serum.

4.1 Synthesis of HABAylated-Sepharose Gel

According to Scheme 8, Sepharose CL-4B hydroxyl functions are first activated as p-NO$_2$ phenyl carbonates as described in WilShek et al, 1984, and the active gel is then coupled to a-tyrosine or to a 3-(2-hydroxyphenyl)alkanoic acid derivative carrying a spacer arm with a primary amine as t he terminal group such as Compound 4, or similar compounds with different spacers A and/or B. The HABA function is then obtained by diazotization of the phenyl residues directly on the Sepharose support (Vetter 1994).

4.1.a Synthesis of Sepharose-tyrosine and Sepharose-Compound 4

A solution of o-tyrosine or Compound 4 in aqueous buffer (35 mM in bicarbonate or borate, pH 8.5) is added to p-NO$_2$-phenyl carbonate-activated Sepharose carrying 50–100 mmoles active groups/g wet gel.

The reaction is carried out on 3–5 g gel in a total volume of 12–15 ml, using a 3:1 molar ratio between the primary amine (o-tyrosine or Compound 4) and the activated groups of the gel. The suspension is gently stirred for 150 minutes at room temperature. The gel is then washed with H$_2$O, MeOH, EtOAc and then, MeOH and water again. Unreacted active groups in the gel are hydrolyzed by 5 minutes exposure to 0.2M NaOH. The gel is washed again and resuspended in 0.2M KOH (3 g/5ml) for the final diazotization step.

4.1.b Synthesis of HABAylated-Sepharose: Diazotization Reaction

Anthranilic acid and NaNO$_2$ are dissolved in H$_2$O (156 mmoles/ml for both) and concentrated HCl 100 l/ml of water) is added after cooling in a ice bath. The solution is stirred for 5 minutes and then added dropwise to the gel suspended in 0.2M KOH (3 g/5ml). The reaction is gently stirred for 15 minutes under temperature control. The pH is monitored constantly and adjusted to 8.0–8.5 using diluted KOH. A molar ratio of 1:1 between anthranilic acid and the phenyl residues in the gel is used, assuming that a complete conversion of the activated p-NO$_2$-phenyl groups occurred in the previous step of the synthesis. The gel is then washed using the procedure as in the previous step and it is finally suspended in PBS.

4.2 Avidin Purification using HABAylated-Sepharose

FIG. 1 shows the elution profiles of avidin from HABAylated-Sepharose obtained according to the method described in 4.1.b above using Compound 4. The gel (100 mg) was incubated for 20 min at room temperature with an avidin solution in PBS (2 mg/ml) and then washed with different eluants. Final elution of avidin was carried out with either 0.3M TEA, pH 11.5 or with a biotin solution in NaHCO$_3$ (1 mg/ml). When the TEA buffer is used, the eluted fractions are immediately neutralized using 1M acetic acid.

Example 5

Anti-HABA Antibodies: Production and Characterization 5.1 Preparation of Immunogenic HABAylated Proteins KLH, BSA, and goat-affinity purified anti-Mouse IgGs were HABAylated using the succinmidyl carbamnate reagent (Compound 17) as the coupling agent by the procedure described in 3.2.b above. Briefly, the coupling agent dissolved in DMF was added to a solution of the protein in 0.1M NaHCO$_3$ (2–10 mg/ml). After 2 hours, the excess of HABA reagent was removed by gel filtration on a G25 column. The degree of coupling could be estimated from the UV spectra of the conjugates, considering the $\epsilon_{356}$ of 12,900 for the HABA-derivative in PBS and measuring the protein concentration by BCA protein assay.

5.2 Preparation of Anti-HABA Polyclonal Antibodies 5.2.a Rabbit Immunization for Anti-HABA Production Rabbits (12 weeks) were immunized by intradermal injection of 0.5 mg of HABA-KLH (carrying ~50 molecules of HABA/protein) emulsified in complete Freund's adjuvant. Boosts were administered after 4 weeks by injecting 0.5 mg of HABA-protein in incomplete Freund's adjuvant. Blood was collected from the ear vein two weeks after boosting and serum was isolated by centrifugation and preserved at −20° C. Preserum was collected before immunization and used as a control.

52.b Affinity Purification of Anti-HABA Polyclonal Antibodies

HABA-Sepharose coupled with Compound 4 with diaminohexane as spacer arm was prepared from Sepharose CL-4B as described above in 4.1.a. The gel was pre-treated with 0.1M TEA pH 11.5 before any farther use and re-equilibrated with PBS. Rabbit antisera diluted 1:1 with PBS were incubated with the gel for 4 hours at 4° C. Total removal of anti-HABA antibodies from supernatant was verified by dot blot on nitrocellulose paper, using BSA-HABA for dotting. In order to obtain an efficient retention of anti-HABA antibodies, a ratio of 1:1 w/w between serum and gel was used. The gel was then washed extensively with 0.05 M Tris HCl, 0.5M NaCl, pH 7.5, and bound antibodies were eluted by basic treatment using 0.1M TEA, pH 11.5. The eluting fractions were immediately neutralized and dialyzed against PBS. Alternatively, the Pierce gentle Ab/Ag elution buffer was used. No significant difference between the antibodies eluted with these two eluants was observed.

5.2.c Characterization of anti-Sera and Affinity Purified anti-HABA Polyclonal Antibodies Both sera and affinity purified antibodies are analyzed for antigen recognition by ELISA assay according to the following protocol: 96-well microtiter plates (Nunc F96 Maxisorp) are coated by overnight incubation at 4° C. with 50 μl/well of a BSA-HABA solution 10 μg/ml in 0.05 M NaHCO$_3$, pH 9.3. Plates are washed three times with PBS/Tween 0.05% (PBS/T) and blocked by adding 200 μl of PBS/T containing 3% BSA. After 2 hours incubation at 37° C., plates are washed three times with PBS/T.

Serial dilutions of anti-sera or affinity purified antibodies (50 μl) are incubated for 2 h at 37° C. The plates washed 3 times with PBS/T are incubated for 2 hours at 37° C. with 50 μl/well of a solution containing HRP-conjugated anti-rabbit antibodies (diluted 1:2500). After extensive washing with PBS/T, 100 μl of ABTS solution are added and the OD. at 405 nm is measured after 30 minutes (Engvall 1980). The purity of the affinity purified anti-HABA polyclonal antibodies is verified by SDS gel electrophoresis.

5.3 Affinity Purification of Anti-HABA Polyclonal Antibodies

Two different Sepharose gels (A and B) were prepared for the isolation of anti-HABA antibodies specific to different epitopes in the HABA molecule. A schematic representation of the two gels is described in Scheme 9.

GEL A is a highly functionalized HABAylated-Sepharose having the correct HABA moiety (4'-hydroxy-azophenyl-2-carboxylic acid linked at position 3') connected with a spacer arm in a similar way as in the HABAylated KLH.

GEL B is a highly functionalized gel having a HABA moiety with a slightly different structure (2'-hydroxy-azophenyl-2-carboxylic acid linked at position 5' via a spacer arm) obtained by diazotization of tyramine-Sepharose with anthranilic acid.

These two gels allow isolation of anti-HABA antibodies with different characteristics: GEL A is able to isolate anti-HABA antibodies that recognize the whole HABA molecule, while GEL B allows the isolation of antibodies that are specific for the azophenyl-2-carboxylic acid moiety of the HABA core.

5.3.a Preparation of GEL A

Sepharose CL-4B hydroxyl functions were first activated as p-nitrophenyl carbonates (Wilchek et al, 1984) and the active gel was then coupled to a 2-hydroxyphenyl derivative carrying a spacer arm with a primary amine as the terminal group. Different spacers can be introduced by varying this first compound. The HABA function was then obtained by diazotization of the phenyl residues directly on the Sepharose support (Vetter et al, 1994).

(i) Sepliarose-tyrosine or 2-Hydroxyphenylpropionyldiamino Hexane.

The primary amines tyrosine or 2-hydroxyphenylpropionyl-diaminohexane dissolved in aqueous buffer (35 mM borate buffer, pH 8.5) were added to the p-nitrophenyl carbonate-activated Sepharose (carrying 50–100 mmoles of active group/g of wet gel).

Reactions were carried out on 3–5 g of gel, in a total volume of 12–15 ml and using a molar ratio of 3:1 between the primary amine and the activated groups of the gel. Suspensions were gently stirred for 150 minutes at room temperature, and the gels were then washed with water, MeOH, EtOAc and then, MeOH and water again. Unreacted active groups in the gel were hydrolyzed by 5 minutes exposure to 0.2M NaOH. Gels were washed again and resuspended in 0.2M KOH (3 g/5 ml) for the final diazotization step.

(ii) Diazotization Reaction.

Anthranilic acid and NaNO2 were dissolved in H$_2$O (156 mmoles/ml for both) and concentrated HCl (100 ml/ml of water) was added after cooling in an ice bath. The solution was stirred for 5 minutes and then added dropwise to the gel suspended in 0.2M KOH (3 g/5 ml). The reaction was gently stirred for 15 minutes, while the temperature was controlled using an ice bath, and the pH was monitored constantly and adjusted to 8.0–8.5 using diluted KOH. A molar ratio of 1:1 between anthranilic acid and the phenyl residues in the gel was used, assuming that a complete conversion of the activated p-nitrophenyl groups occurred in the previous step of the synthesis. The GEL A obtained was then washed (same procedure as in previous step) and suspended in PBS.

5.3.b Preparation of GEL B

Hydroxyl groups of Sepharose CL-4B were first activated with N,N'-disuccinimidyl-carbonate (Wilchek and Miron, 1985), and the activated gel was then coupled to tyramine via the amino group. The HABA derivative was obtained by diazotization of the phenyl residues using anthranilic acid.

(i) Sepharose-tyramine

Tyramine dissolved in PBS (pH 7.4) was added to the N,N'-disuccinimidylcarbonate activated Sepharose (carrying 20–80 mmoles of active grouping of wet gel). Reactions were carried out on 3–5 g of gel, in a total volume of 12–15 ml and using a molar ratio of 5:1 between the primary amine and the activated groups of the gel. Suspensions were gently stirred overnight at 4° C. Gels were then washed extensively until no more free amine could be detected and unreacted active groups in the gel were hydrolyzed by 5 minutes exposure to 0.2M NaOH. Gels were washed again and resuspended in 0.2M borate buffer (pH 8.5) (3 g/5 ml) for the final diazotization step.

(ii) Diazotization Reaction.

Anthranilic acid and $NaNO_2$ were dissolved in $H_2O$ and concentrated 0.2M HCl was added after cooling in a ice bath. The solution was stirred for 5 minutes and then added dropwise to the gel suspended in 0.2M borate buffer (3 g/5 ml). The reaction was gently stirred for 15 minutes, while the temperature was controlled using an ice bath and the pH monitored constantly and adjusted to 8.0–8.5 using diluted KOH. A molar ratio of 1:1 between anthranilic acid and the phenyl residues in the gel was used, assuming that a complete conversion of the activated p-nitrophenyl groups occurred in the previous step of the synthesis. The GEL B obtained was then washed and finally suspended in PBS.

5.3.c Affinity Purification of Anti-HABA Polyclonal Antibodies with GEL A and GEL B.

Sepharose GELS A and B were pre-treated with 0.1M TEA pH 11.5 before any further use and re-equilibrated with PBS. Rabbits' antisera diluted 1:1 with PBS or IgG antibodies obtained by $(NH_4)_2SO_4$ precipitation were incubated with the gel for 4 hours at 4° C. Total removal of anti-HABA antibodies from supernatant was verified by dot blot on nitrocellulose paper, using BSA-HABA for dotting. In order to obtain an efficient retention of anti-HABA antibodies, a ratio of 1:1 w/w between serum and gel was used. The gel was then washed extensively with 0.05 M Tris HCl, 0.5M NaCl, pH 7.5. Bound antibodies were finally eluted by basic treatment, using 0.1M TEA, pH 11.5, immediately neutralized and dialyzed against PBS.

53.3.d Characterization of Anti-sera and Affinity Purified Anti-HABA Polyclonal Antibodies: Screening for Anti-HABA Antibodies with Different Specificities.

Purity of the affinity purified anti-HABA polyclonal antibodies according to Example 5.3.c above was verified by SDS gel electrophoresis. Concentration of an affinity purified anti-HABA antibody solution was determined spectrophotometrically using the average $\epsilon^{\%}_{280\ nm}$ value of 14.5 for IgGs. Specificity of anti-sera and affinity purified antibodies for different epitopes in the HABA molecule was verified by ELISA and UV spectrophotometry.

5.3.e ELISA Assay

Ninety-six well microtiter plates (Nunc F96, Maxisorp) were coated by overnight incubation at 4° C. with 50 µl/well of HABAylated avidin solution (10 µg/ml in 0.05 M Na carbonate, pH 9.5). Plates were washed three times with PBS/Tween 0.05% (PBS/T) and blocked by adding 200 µl of PBS/T containing 3% BSA or 0.1% of gelatine. After 2 hours incubation at 37° C., plates were washed three times with PBS/T.

Serial dilutions of antisera or affinity purified anti-HABA antibodies (50 µl) were then incubated for 2 h at 37° C. When HABAylated avidin was used for the coating, the experiment was run in duplicate and the antibodies were incubated with and without biotin in the diluting buffer. Plates were washed 3 times with PBS/T and incubated for 2 hours at 37° C. with 50 µl/well of a solution containing HRP-conjugated anti-rabbit antibodies (diluted 1:2,500). After extensive washing with PBS/T, 100 µl of o-phenylenediamine solution were added, the reaction stopped using 1M $H_2SO_4$ and the OD at 490 nm was measured after 5 minutes.

Absence of cross reactivity against the anthranilic part of the HABA molecule was verified running a control ELISA assay with BSA-anthranilic acid in the first coating. As shown in FIG. 1, anti-HABA antibodies purified on GEL A were able to recognize HABA as part of the HABAylated avidin in the absence (◇) as well as in the presence of biotin (◆). However, in the absence of biotin, the anti-HABA antibody purified on GEL B failed to recognize the HABA buried in the binding site. Upon addition of biotin, however, the HABA moiety was expelled and strong binding of the anti-HABA antibody was detected (●). This effect clearly depends on the procedure used for purification of the anti-HABA antibodies.

5.3.f Spectrophotometry

UV spectra of HABA (compound 0) in PBS was recorded in the presence of the anti-HABA antibodies affinity purified in both GELs A and B. The results indicate that:

Antibodies purified with GEL A (A-anti-HABAs) recognize the HABA moiety when it is either in the azo or the quinone conformation. Antibodies purified with GEL B (B-anti-HABAs) can bind to the HABA moiety only when it is in the azo conformation whereas they fail to recognize it in the quinone conformation. In this case, recognition of the HABAylated avidin occurs only after biotin expels HABA from the binding pocket.

5.4 Preparation of Anti-HABA Monoclonal Antibodies

5.4.a Hybridoma Production

A HABA-KLH conjugate prepared as described above and carrying ~100 molecules of HABA/protein was used for the immunization. Five Balb/c mice were first injected into the foot pads with a pure preparation of the HABA-KLH (2.5 mg/mouse, emulsified in a complete Freund's adjuvant) and two weeks later subcutaneously in incomplete Freund's adjuvant. Two additional injections were given at two weeks interval, subcutaneously, in PBS. The mouse chosen for fusion received an intraperitoneal injection of the immunogen, followed the day after by an intravenous one. Three days after the i.v. injection, lymphocites from the spleen and the inguinal lymph nodes ($192 \times 10^6$ cells) were fused with $50 \times 10^6$ NSO/1 myeloma variant (NSO cells, kindly provided by C. Milstein, MRC, Cambridge, U.K.) by standard techniques. The fused cells (hybridomas) were distributed into 16-microculture plates (~$3 \times 10^4$ cells/well). Hybridomas that were found to secrete anti-HABA antibodies were cloned and recloned by the limiting dilution technique. The immortalized hybridomas selected after the screening were frozen and used later for a large scale preparation of pure anti-HABA monoclonal antibodies.

5.4.b Screening Methods for Hybridoma Selection

In order to isolate anti-HABA hybridomas with desired characteristics, namely (i) high affinity and specificity for the 'HABA core' of the antigen, thus reducing the influence of the spacer arm in the recognition process, and (ii) high affinity and specificty for the whole Compound 17 (HABA+ spacer arm), for isolation of an antibody that recognizes the molecule only when the spacer arm is present, two well-known screening techniques were used: 'direct' and competitive ELISA.

For preliminary screening, a direct binding assay as described for polyclonal antibodies testing in 5.2.c was used, except that single hybridoma culture supernatant was used for the serial dilutions instead of anti-sera, and HRP-conjugated anti-mouse antibodies (Peroxidase-conjugated AffiniPure Goat Anti-Mouse IgG (H+L) diluted 1:5,000) were used for detection.

The hybridomas that showed the best response in this general ELISA test were selected for further screening by competitive ELISA assay: 96-well microtiter plates (Nunc F96 Maxisorp) were coated by overnight incubation at 4° C. with 50 μl/well of a BSA-HABA solution 10 μg/ml in 0.05 M NaHCC$_3$, pH 9.3. Plates were washed three times with PBS/Tween 0.05% (PBS/T) and blocked by adding 200 μl of PBS/T containing 3% BSA. After 2 hours incubation at 37° C., plates were washed three times with PBS/T.

The BSA-HABA coated plates were then incubated for 2 h at 37° C. with diluted hyridoma supernatant together with different amounts of three HABA-derivatives (0.1–1 mg in a final volume of 50 μl): Compound 0 (HABA), Compound 16 with A=(CH$_2$)$_2$, and analog of Compound 16 with A=CH=CH. The hybridoma dilutions were chosen according to the results of the preliminary direct binding assay in order to have approximately the same response in the ELISA for all the hybridoma tested and corresponding to 50% of the maximal response.

Plates were then washed 3 times with PBS/T and incubated for 2 hours at 37° C. with 50 μl/well of a solution containing HRP-conjugated anti-mouse antibodies (1:5,000). After extensive washing with PBS/T, 100 μl of ABTS solution were added and the O.D. at 405 nm was measured after 30 minutes.

Hybridomas giving the desired results, e.g. 745.7, 913.1 and 915.65 were afterwards selected for further preparation of supernatent.

5.4.c Labeling of Anti-HABA Antibodies

Different labels can be introduced in the HABA-binding molecules, i.e. avidin and anti-HABA antibodies, for the visualization of the HABA/anti-HABA complexes. Color enzymes, colored, fluorescent and chemiluminescent probes can be covalently bound by using general labeling protocols as described elsewhere (Garman, 1997).

Example 6

DNA AND RNA Technology 6.a HABAylated Nucleotides

HABAylated nucleotides, which are suitable substrates for DNA and RNA polymerases in vitro, can be synthesized from the amino reactive HABA-Su derivatives, such as for example Compounds 17, 21 and 28, and the aminoallyl derivatives of the nucleotides, in a similar way as described for biotin-nucleotides (Langer, 1981; Shinikus, 1986).

6.b Labeling of Oligonucleotides With HABA

The HABA derivatives that are reactive towards primary amino groups, such as for example Compounds 17, 21 and 28, can be used for chemical labeling of amino functionalized short oligonucleotides as described for biotin and DIG labels (Garman, 1997). The HABA probes can be introduced at the 3' or 5' end or in the middle region of the obgonucleotide, depending on the strategy used for the introduction of the amino functions during the oligo synthesis. Alternatively, the thiol reactive HABA-derivative (Compound 18) can be used in thiol functionalized oligonucleotides.

6.c Labeling of Long Nucleic Acid Probes

DNA and RNA labeling can be achieved either enzymatically or chemically. Similar strategies and methods as those already in use for tagging nucleic acid with biotin or DIG can be used (Kessler, 1995; Garman, 1997).

PCR, nick translation and random primer methods can be applied for DNA labeling using HABAylated nucleotides. RNA polymerase can be used for RNA molecules.

Example 7

Applications of the HABA/Anti-HABA Technology

The HABA core of the HABA-derivatives of the invention can be recognized by both avidin and specific anti-HABA antibodies, leading to a color change from yellow to red in the chromophore. Such interactions occur also when the HABA-derivatives are covalently bound to any surface or protein. Thus, if the HABA compound is covalently bound to a protein or to a DNA or RNA that is used as a 'binder' in a specific bioassay or bioapplication, the interaction with the target can be monitored with the use of either avidin or anti-HABA antibodies.

Visualization and quantification of the HABA/avidin or HABA/anti-HABA complex can be carried out in two different ways: (i) preferably, using avidin or anti-HABA antibodies labeled by well-known methods of non-radioactive and radioactive labeling such as fluorescence, chemiluminescence, enzymatic label, etc., by the same procedures used in the avidin/biotin or the DIG/anti-DIGtechnologies The choice of these labels will depend on the need of the users and on the technology chosen (Garman, 1997); or (ii) by measuring the HABA color change that occurs after recognition with a regular UV-Vis spectrophotometer that can detect the complexed HABA molecule in solution up to micromolar concentrations, or with more sophisticated technologies that can be used for quantification of even lower concentrations.

The interaction of avidin with HABA is weaker than the avidin/biotin interaction. After the HABA/avidin complex is formed, the avidin molecule can be displaced by addition of a biotin solution and the HABAylated probe can be monitored with the second independent method, by using the anti-HABA antibody system.

For the visualization of the target/binder complex, in a typical experiment, the HABAylated binder II such as an antibody, lectin, DNA or RNA, is added to a preparation such as a cell preparation, a DNA or protein blot, containing the target molecule I, e.g. the antigen, the carbohydrate and so on. After the complex HABAylated binderII/target molecule I is formed, the excess of HABAylated probe II is removed and avidin or anti-HABA antibodies (labeled or unlabeled) are applied. Visualization will depend on the application and the type of label used.

When nonlabeled avidin or anti-HABA antibodies are used, the HABA color change can be used for complex visualization, but this detection system is not very sensitive ($\epsilon_{500\ nm}$ of bound HABA is about 30,000). Labeled anti-HABA antibodies or avidin, for example with fluorescent, chemiluminescent, radioactive or color enzymatic labels, allow a higher sensitivity. In this case, detection of the target molecule will depend on the type of label used.

If avidin (labeled or not labeled) is used for detection, after visualization a biotin solution can be applied to remove the colored probe, and then anti-HABA antibodies (labeled or not labeled) can be applied for a second visualization. Parallel analysis with the two detection systems can also be carried out if enough sample is available.

If non-labeled antibody or avidin is used, a labeled second antibody or labeled anti-avidin antibody can be added for visualization.

Since the interaction with anti-HABA antibodies is stronger than the one with avidin, the anti-HABA technology is recommended when high sensitivity is needed.

The anti-HABA technology can be applied to any of the analytical techniques presently in use in biochemistry, molecular and cell biology in a similar way as biotin and DIG are used for radioactive or non-radioactive labeling.

In molecular and cell biology, hybridization with HABAylated RNA or DNA probes can be carried out for 'in situ' studies or for blot analysis. Application of these techniques is very wide, including diagnosis (viruses, bacteria, genetic diseases), chromosome mapping, gene localization, gene expression, cell apoptosis detection.

Other analytical tools that use radioactive or non-radioactive labeling and that can take advantage of the HABA technology are glycoprotein sugar analysis and classical immunoassays (e.g. ELISA). HABAylated molecules can also be immobilized to solid supports for affinity chromatography or phage display screening as in the avidin/biotin technology.

In molecular and cell biology, this technique can be used, for example, in blotting:

Southern blot: In order to identify the presence of a specific gene in a DNA sample, a HABAylated probe can be used: the DNA is previously digested with specific restriction enzyme and is subjected to agarose electrophoresis. DNA is then transferred to a specific membrane (nylon, nitrocellulose or activated paper) and hybridized with the HABAylated complementary DNA. The anti-HABA detection system as described above can be used to visualize the desired band.

Northern blot: Hybridization with HABAylated probes can be carried out in a similar way as for Southern blot. RNA molecules, e.g. mRNAs, are separated by agarose electrophoresis, transferred to a specific membrane and hybridized with the HABAylated DNA or RNA probes. Hybridized molecules can be visualized using the anti-HABA technology previously described.

A further application of this technology is in chromosome mapping: HABAylated ssDNA or RNA probes complementary to the target genes can be used for hybridization to metaphase chromosome spreads. After washing off the excess of HABAylated probes, fluorescent or chemiluminescent anti-HABA antibodies are added and, after washing, the locus of hybridization can be localized by light or fluorescent microscopy. This technique allows to visualize the location of specific genes within, or inside, specific chromosomes.

A still further application of this technology is in mRNA expression in specific tissues in situ hybridization hystochemistry. Cellular localization of mRNAs can be visualized using specific HABAylated riboprobes: the HABAylated RNA complementary to the target mRNA can be hybridized with the tissue under examination. Hybridization can be visualized with the anti-HABA system using light or fluorescent microscopy. This methodology is used for localization or expression studies of specific mRNAs, either in different tissues or in different types of cells within a single tissue.

Yet a further application of this technology is in the visualization of apoptotic cells. Terminal transferase-mediated d-UTP-HABA nick end labeling (TUNEL) can be used to 3'-end-label fragmented DNA in order to visualize apoptotic cells which are characterized by a highly segmented DNA. This DNA can be 3' end labeled with a HABAylated nucleotide, and the HABAylated ends are detected by the anti-HABA system. Visualization is carried out using light or fluorescent microscopy whereby the apoptotic cells result very intensely marked as compared to normal ones.

In lectin cytochemistry, lectin conjugates with HABA and labeled anti-HABA/avidin are used for light or electron microscopy detection of glycoconjugates in tissue sections. The HABAylated lectins are applied to the tissue section and labeled anti-HABA/avidin are applied. The interaction can be visualized either by electron or light microscopy.

A further application of the technology of the present invention is in diagnosis, for example in genome incorporated viruses (DNA or RNA), slow replicating bacteria and genetic diseases.

a. Genome Incorporated Viruses (DNA or RNA): In situ hybridization of DNA or RNA of the target virus pathogen with specific HABAylated probes can be carried out inside infected cells. The cells are incubated with the specific HABAylated DNA or RNA probe and, after washing, hybridization can be visualized after labeled avidin/anti-HABA application. Visualization can be achieved using a light or electron microscope.

b. Slow replicating bacteria: Hybridization techniques can also be useful for the identification of certain bacteria from patients' specimen such as slow replicating bacteria, e.g. Mycobacterium Tubercolosis, or bacteria difficult to identify with common kits. Bacteria DNA can be identified by hybridization with specific HABAylated DNA or RNA probes. The patient specimen is first treated in order to allow contact between probe and target, e.g. cell treatment with proteinase K, SDS, etc. Visualization can be carried out with a microscope after hybridization with the avidin/anti-HABA system and washing off the unbound probes.

c. Genetic diseases: The same principles as those described for chromosome mapping can be used for diagnosis of genetic-related diseases and prenatal diagnosis. HABAylated DNA probes complementary to specific genes or gene sequences are hybridized to the chromosome spread. Hybridization is visualized after anti-HABA system application, using fluorescent or chemiluminescent labeling and microscopic visualization.

In biochemistry, the technology of the present invention can be used in Western blotting, ELISA assays, and glycoprotein sugar analysis.

For Western blotting, SDS-PAGE is carried out in the protein mixture and Western immunoblot is carried out to transfer the proteins to a specific membrane. After blocking the uncoated sites, HABAylated antibodies can be introduced. Detection is carried out as described above using labeled avidin or anti-HABA antibodies.

For ELISA assay, a biological solution, e.g. cell extract, containing the target molecule, is used to coat the ELISA plate. After blocking the uncoated sites, HABAylated anti-target antibodies are applied. After washing, enzyme-labeled avidin or anti-HABA antibodies are incubated and enzyme color development is carried out for visualization and quantification.

For glycoprotein sugar analysis, i.e. for analysis of the type of glycosylation of a glycoprotein, a similar approach as the one described above for the ELISA test can be used. The purified glycoprotein is absorbed on the microtiter plate surface and, after removing the unbound protein and quenching of the uncoated sites, HABAylated specific lectins are applied. After washing, the degree of lectin binding is measured using either labeled anti-HABA antibodies or labeled avidin.

Other application envisaged by the present invention refers to drug delivery studies whereby HABAylated oligonucleotides can be used to follow the fate of oligonucleotides in drug delivery studies for gene or anti-sense therapy applications (Lappalainen, 1997).

Appendix I
STRUCTURES OF COMPOUNDS 0–29

0 HABA

1 [A] = (CH$_2$)$_2$

2 [A] = (CH$_2$)$_2$

3 [A] = (CH$_2$)$_2$; [B] = (CH$_2$)$_6$

4 [A] = (CH$_2$)$_2$; [B] = (CH$_2$)$_6$

5 [A] = (CH$_2$)$_2$; [B] = (CH$_2$)$_6$

6 [A] = (CH$_2$)$_2$; [B] = (CH$_2$)$_6$ [B′] = (CH$_2$)$_3$

7 [A] = (CH$_2$)$_2$; [B] = (CH$_2$)$_5$

8 [A] = (CH$_2$)$_2$; [B] = (CH$_2$)$_5$

9 [A] = (CH$_2$)$_2$

10 [A] = (CH$_2$)$_2$; [B] = (CH$_2$)$_6$

11 [A] = (CH$_2$)$_2$; [B] = (CH$_2$)$_5$

12 [A] = (CH$_2$)$_2$; [B] = (CH$_2$)$_5$

13 [A] = (CH$_2$)$_2$

-continued
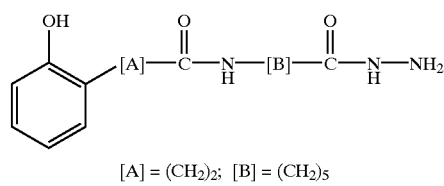
[A] = (CH$_2$)$_2$; [B] = (CH$_2$)$_5$
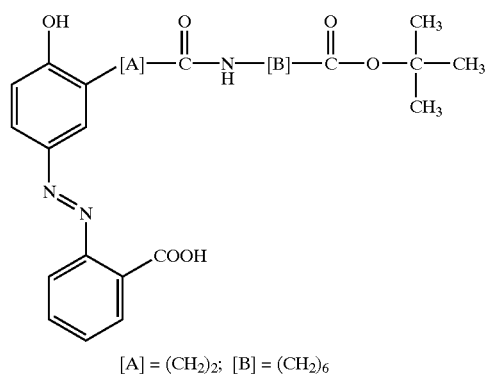
[A] = (CH$_2$)$_2$; [B] = (CH$_2$)$_6$
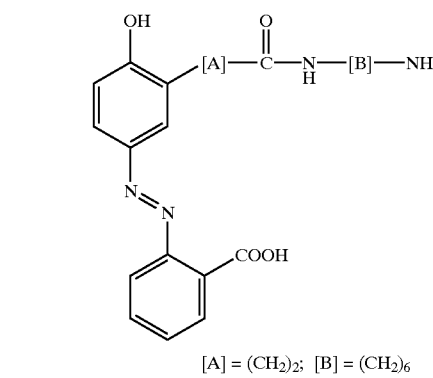
[A] = (CH$_2$)$_2$; [B] = (CH$_2$)$_6$
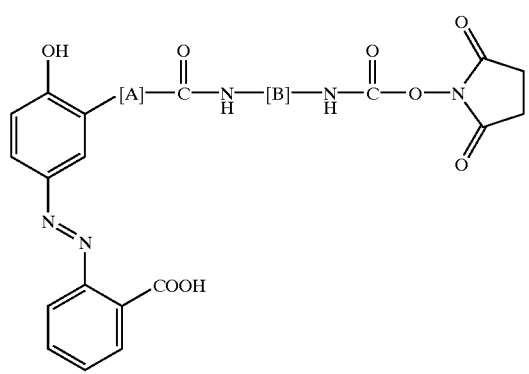
[A] = (CH$_2$)$_2$; [B] = (CH$_2$)$_6$
-continued
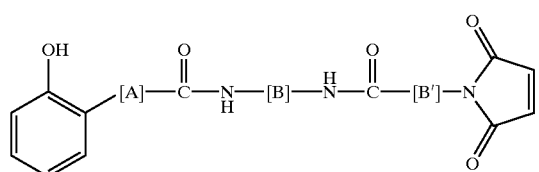
[A] = (CH$_2$)$_2$; [B] = (CH$_2$)$_6$; [B'] = (CH$_2$)$_3$
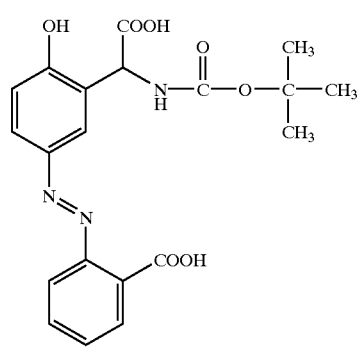
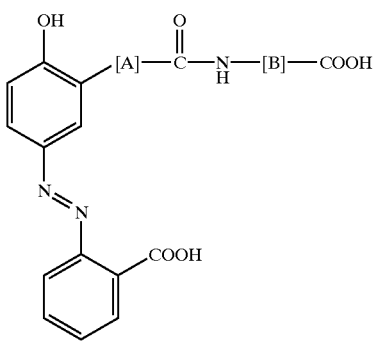
[A] = (CH$_2$)$_2$; [B] = (CH$_2$)$_5$
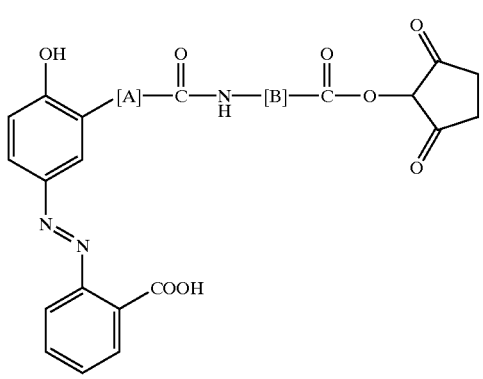
[A] = (CH$_2$)$_2$; [B] = (CH$_2$)$_5$ -continued
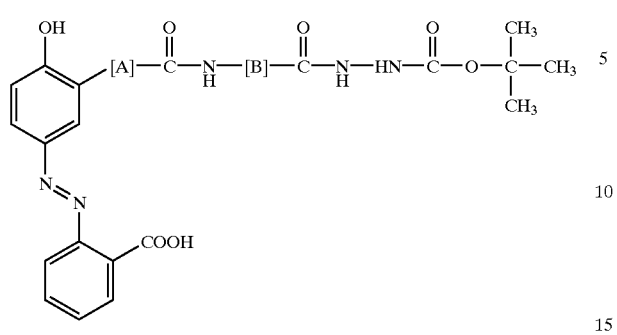
22
[A] = (CH₂)₂; [B] = (CH₂)₅
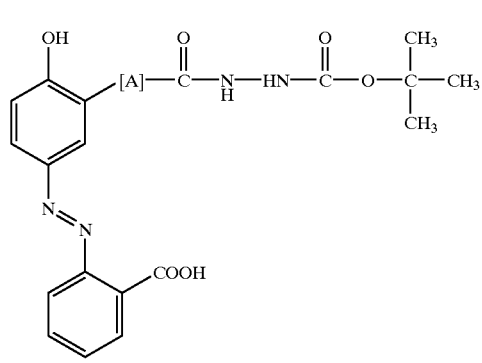
23
[A] = (CH₂)₂
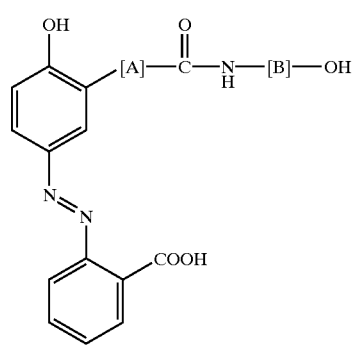
24
[A] = (CH₂)₂; [B] = (CH₂)
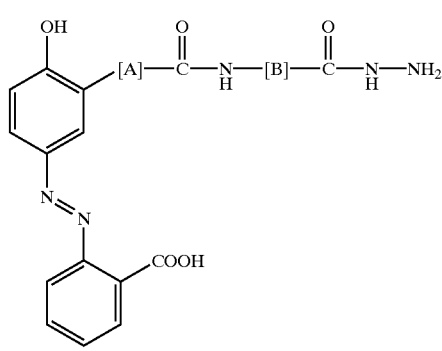
25
[A] = (CH₂)₂; [B] = (CH₂)₅
-continued
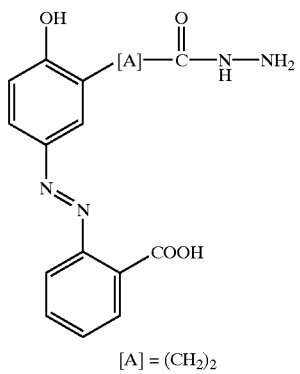
26
[A] = (CH₂)₂
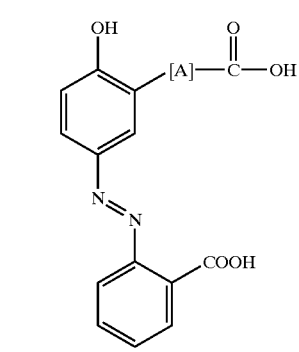
27
[A] = (CH₂)₂
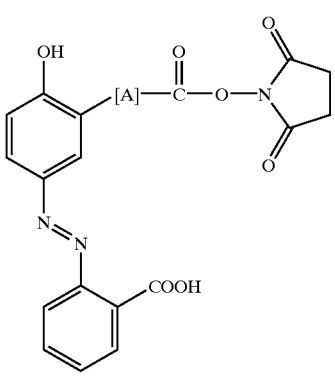
28
[A] = (CH₂)₂
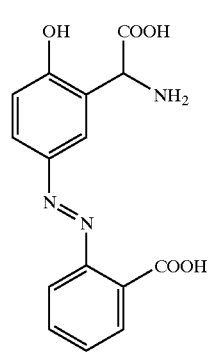
29

Scheme 1
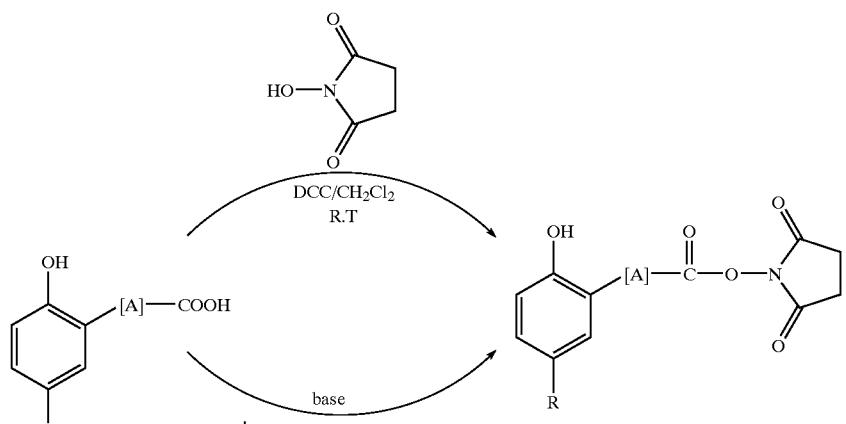
R = —H
or = 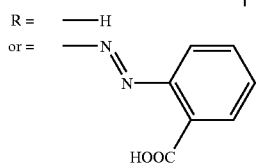
A = —(CH$_2$)$_n$
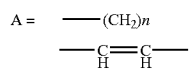
Scheme 2
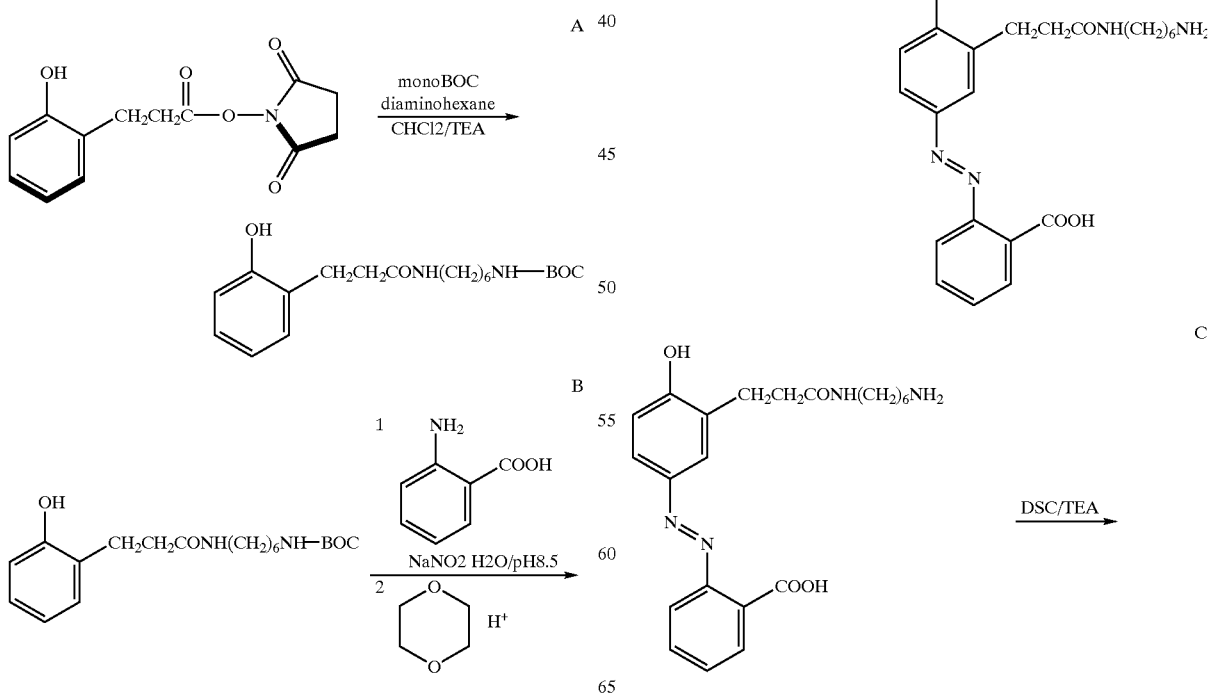
-continued 29
-continued
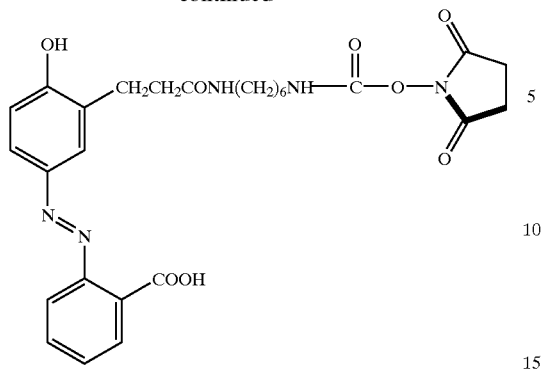
Scheme 4
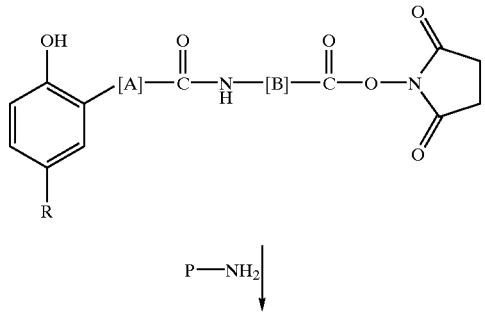
↓ P—NH₂
30
Scheme 3
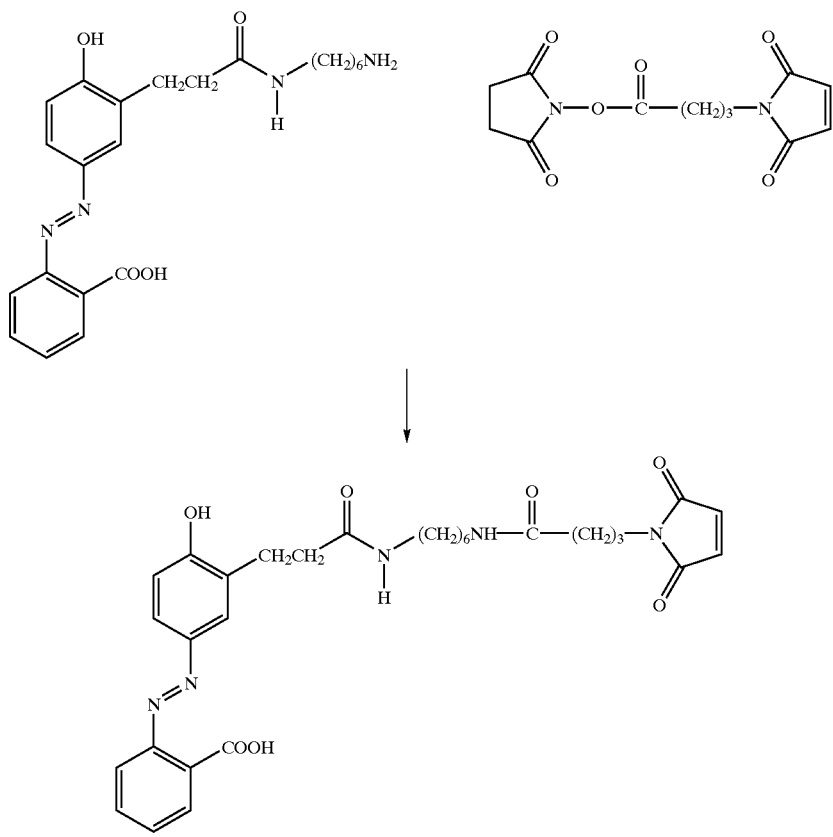
-continued
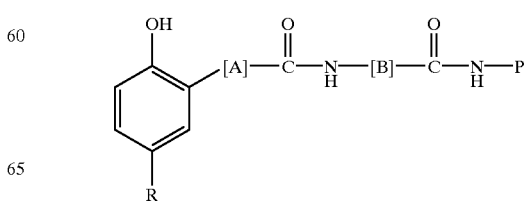

Scheme 6
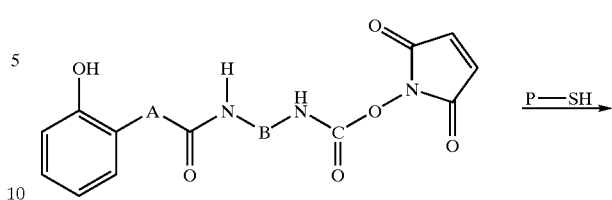
Scheme 5
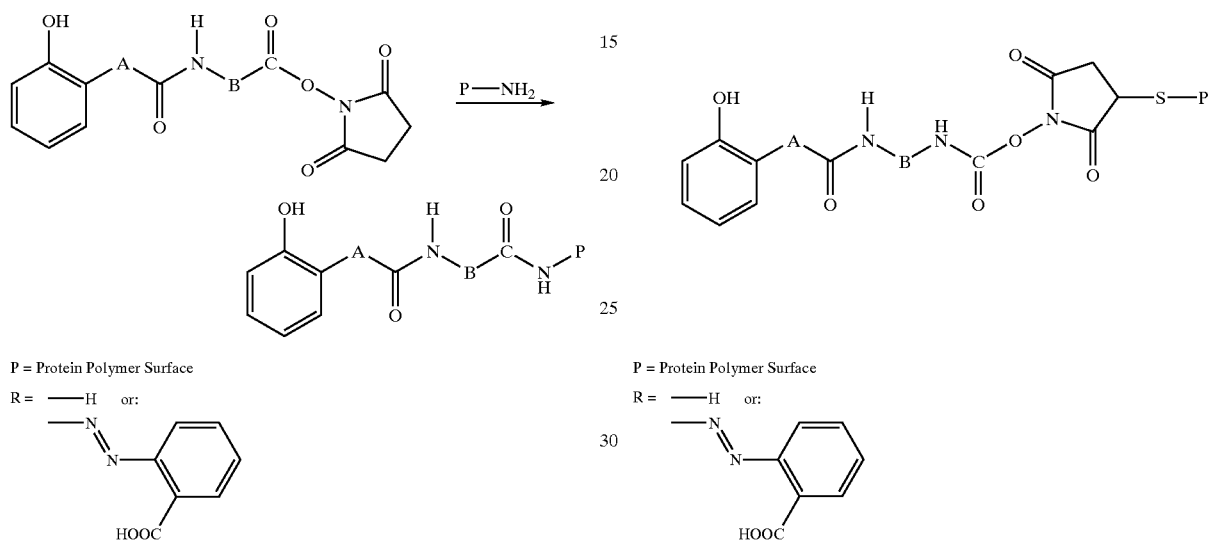
Scheme 7
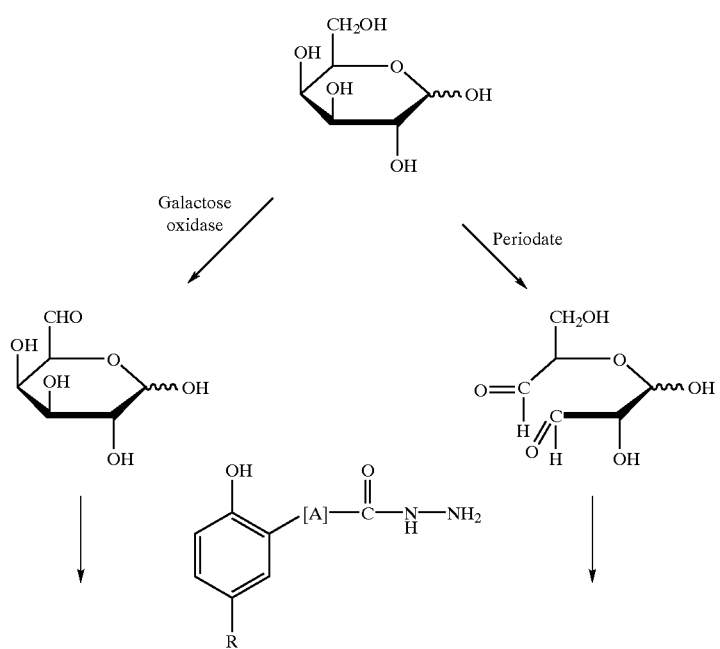

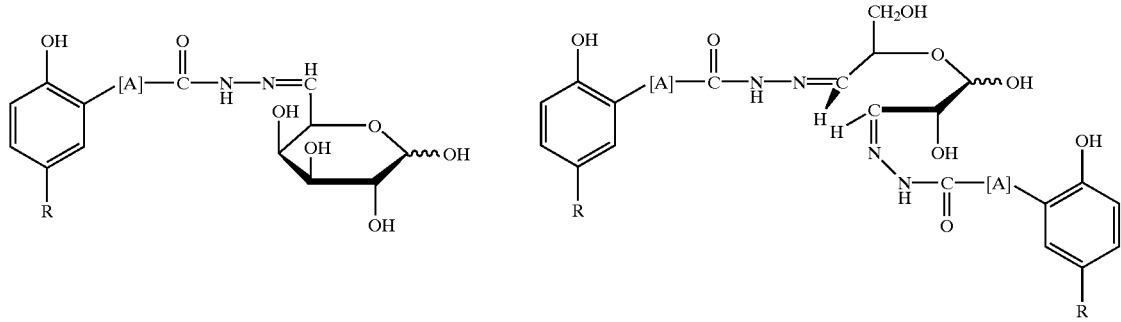
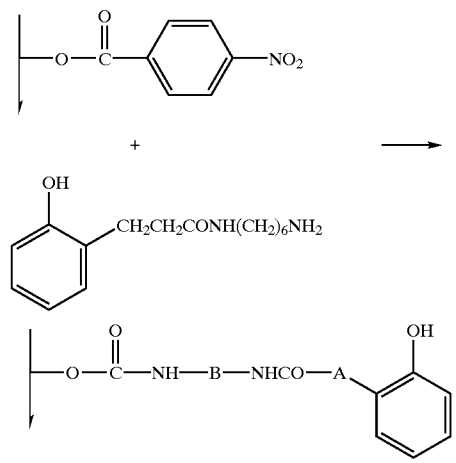
Scheme 8
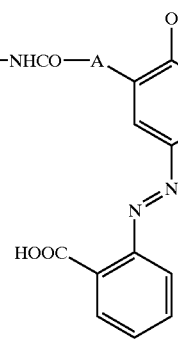
Scheme 9
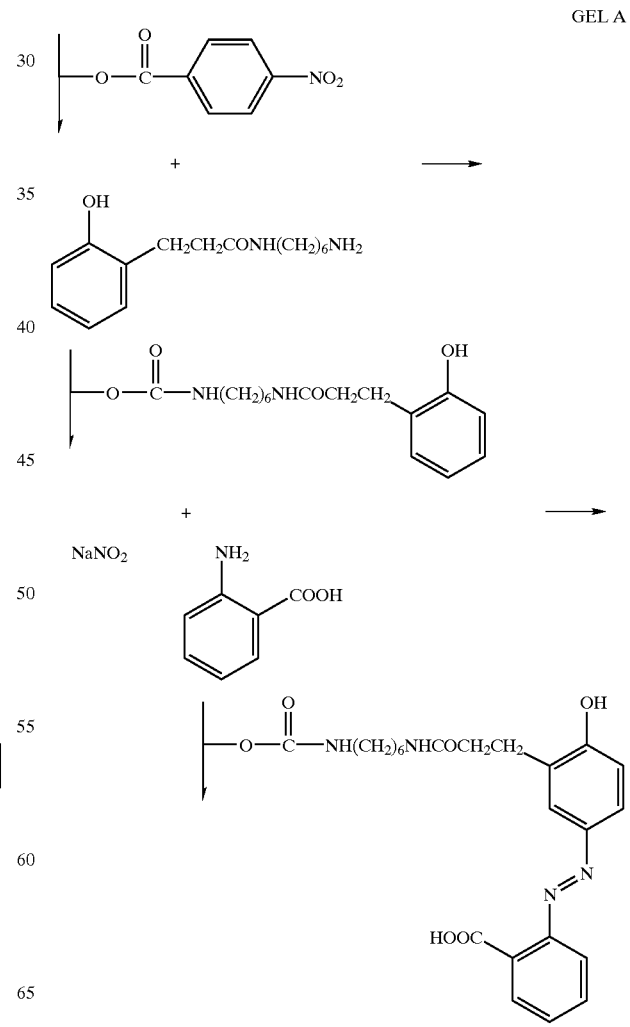
GEL A

-continued

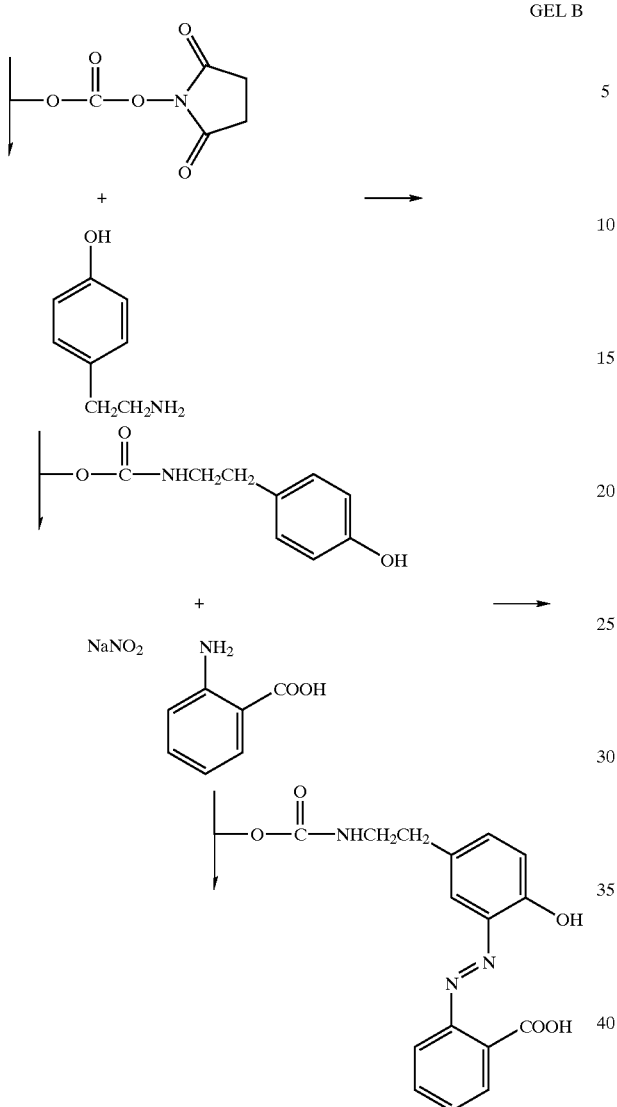

GEL B

REFERENCES

Bannwarth W. and Knorr R., Formation of Carboxamides with N,N,N', N'-Tetramethyl-(succinimido)uronium tetrafluoroborate in aqueous/organic solvent systems, *Tetrahedron Lett.* 32 (1991) 1157.

Engvall E., Enzyme Immunoassay ELISA and EMIT, *Meth Enzymol.* 70, 419 (1980).

Gannan A., Non-Radioactive Labeling, Academic Press, 1997.

Gosh A. K. et al., N,N'-Disuccinimidyl Carbonate: A Useful Reagent for Alkoxycarbonylation of Amines, *Tetrahedron Lett.* 33, 2781 (1992).

Kessler C., Methods for nonradiaoctive labeling of nucleic acids in Non-radioactive probing, blotting, sequencing (ed. L. J. Kickca), Academic Press, 1995.

Kitagawa T. et al., Preparation and Characterization of Hetero-bifinctional Cross-linking Reagents for Protein Modification, *Chem. Pharm. Bull.* 29, 1130 (1981).

Langer P. R, Waldrop A. A., Ward D. C., Enzymatic synthesis of biotin-labeled polynucleotides: Novel nucleic acid affinity probes, *Proc. Natl. Acad. Sci. USA* 78, 6633 (1981).

Lappalainen K. al., Intracellular distribution of oligonucleotide delivered by cationic liopsomes: light and electron microscopy study, *J. Hislochem. Cytochm.* 45, 265 (1997).

Shirnkus M. L, Guaglianone P., Herman T. M., Synthesis and characterization of biotin-labeled nucleotide analogs, *DNA* 5 (3) 247 (1986).

Takeda K. et al., Convenient Methods for Syntheses of Active Carbamates, Ureas and Nitrosoureas usimig N,N'-disuccinimido Carbonate (DSC), *Tetrahedron Lett.* 24, 4569 (1983).

Takeda K., Ogura H., Studies on Heterocyclic Compounds XLIII. Insertion Reaction of Carbonyl groups using Disuccinimido carbonate (DSC), *Synth. Commun.* 12, 213 (1982).

Vetter S., Bayer E. A. and Wilchek M., Avidin can be forced to adopt catalytic activity, *J. Am. Chem. Soc.* 116, 9369 (1994).

Wichek M., Miron T., Kohn J., Affinity Chromatography, *Meth Enzymol.* 104, 3, (1984).

Wilchek M. and Bayer E. A., Labeling of glycoconjugates with hydrazide reagents, *Meth. Enzymol.* 138, 429 (1987).

What is claimed is:

1. A compound of formula

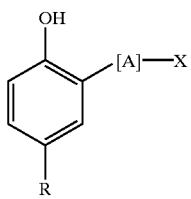

wherein

R is —N=N-2-carboxyphenyl;

A is $(CH_2)_n$, —CH(COOH)— or —CH=CH—, wherein n is an integer from 0 to 10; and X is a radical selected from the group consisting of:
  (i) Cl;
  (ii) $COOR_1$, wherein $R_1$ is H, p-nitrophenyl or N-succinimidyl;
  (iii) CONH—$NHR_2$, wherein $R_2$ is H, COO(t-butyl) or COObenzyl;
  (iv) CONH—[B]—$NHR_3$, wherein $R_3$ is H, $COOR_1$, or CO—[B']-maleimido, wherein $R_1$ is t-butyl, p-nitrophenyl or N-succinimidyl, and B and B', the same or different, are $(CH_2)_n$ wherein n is an integer from 2 to 10;
  (v) CONH—[B]—$COOR_4$, wherein B is as defined in (iv) above and $R_4$ is H, $C_1$–$C_8$ alkyl, N-succinimidyl;
  (iv) CONH—[B]—OH, wherein B is as defined in (iv) above;
  (vii) CONH—[B]—CONH—$NHR_2$, wherein B is as defined in (iv) above and $R_2$ is H, COO(t-butyl) or COObenzyl; and
  (viii) $NHR_2$, wherein $R_2$ is H, COO(t-butyl) or COObenzyl, when A is —CH(COOH)— and R is —N=N-2-carboxyphenyl.

2. A HABA compound according to claim 1, wherein A is $(CH_2)_n$ and n is 2 to 4, B is $(CH_2)_5$ or $(CH_2)_6$ and B' is $(CH_2)_3$.

3. A HABA compound according to claim 2, wherein A is $(CH_2)_n$ and n is 2.

4. The HABA compound according to claim 3, being selected from the group of compounds consisting of:
  3'-(6-t-butoxycarbonylamino)hexylaminocarbonylethyl-4'-hydroxy-azobenzene-2-carboxylic acid 3'-(6-aminohexylaminocarbonylethyl)-4'-hydroxy-azobenzene-2-carboxylic acid 3'-(6-(succinimidyloxycarbonylamino)hexylaminocarbonylethyl)-4'-hydroxy-azobenzene-2-carboxylic acid.

3'-(6-(maleimidopropylcarbonylamino)hexylaminocarbonylethyl)-4'-hydroxy-azobenzene-2-carboxylic acid 3'-(1'-carboxy-t-butoxycarbonylaminomethyl)-4'-hydroxy-azobenzene-2-carboxylic acid 3'-(5-carboxypentylaminocarbonylethyl)-4'-hydroxy-azobenzene-2-carboxylic acid 3'-(5-succinimidyloxycarbonylpentylaminocarbonylethyl)-4'-hydroxy-azobenzene-2-carboxylic acid 3'-(5-t-butyloxycarbonylhydrazinocarbonylpentylaminocarbonylethyl)-4'-hydroxy-azobenzene-2-carboxylic acid 3'-(t-butyloxycarbonylhydrazinocarbonylethyl)-4'-hydroxy-azobenzene-2-carboxylic acid 3'-(6-hydroxyhexylaminocarbonylethyl)-4'-hydroxy-azobenzene-2-carboxylic acid 3'-(5-(hydrazinocarbonyl)pentylaminocarbonylethyl)-4'-hydroxy-azobenzene-2-carboxylic acid 3'-(hydrazinocarbonylethyl)-4'-hydroxy-azobenzene-2-carboxylic acid 3'-(carboxyethyl))-4'-hydroxy-azobenzene-2-carboxylic acid 3'-(succinimidyloxycarbonylethyl)-4'-hydroxy-azobenzene-2-carboxylic acid.

5. The HABA compound according to claim 1, wherein A is —CH(COOH).

6. The HABA compound of claim 5, being 3'-(1-carboxy-1-amino-methyl)-4'-hydroxy-azobenzene-2-carboxylic acid.

7. A conjugate of a compound according to claim 1, with a carrier (herein HABAylated compounds), wherein said carrier is a protein, a polypeptide, an amino-carrying polymer, a polynucleotide, an oligonucleotide, a polysaccharide, an oligosaccharide or a compound containing a sugar molecule, and wherein said protein, polypeptide, amino-carrying polymer, or said polynucleotide and oligonucleotide as aminoallyl derivative, or said oligonucleotide as amino functionalized derivative, is bound through a free amino group to said HABA compound that has been activated as N—Su carbamate (—NH—CO—O—Su) or N—Su ester (—CO—O—Su), or said protein or peptide is bound through the SH group of a cysteine residue to said HABA compound that has been functionalized with a terminal maleimido group, or said protein, polysaccharide, oligosaccharide or said compound containing a sugar molecule is bound through an aldehyde residue to said HABA compound that has been functionalized with a terminal hydrazido group.

8. A conjugate according to claim 7 selected from HABAylated cytokines, antibodies, hormones, receptors, DNA, DNA probes, and oligonucleotides.

9. The HABAylated compound according to claim 7, wherein said compound containing a sugar molecule is a glycoprotein.

* * * * *